(12) United States Patent
Shi et al.

(10) Patent No.: US 9,777,028 B2
(45) Date of Patent: Oct. 3, 2017

(54) CO-CRYSTALS, SALTS AND SOLID FORMS OF TENOFOVIR ALAFENAMIDE

(71) Applicant: Gilead Sciences, Inc., Foster City, CA (US)

(72) Inventors: Bing Shi, Redwood City, CA (US); Zhuoyi Su, Edmonton (CA); Fang Wang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/181,213

(22) Filed: Jun. 13, 2016

(65) Prior Publication Data

US 2016/0368938 A1     Dec. 22, 2016

Related U.S. Application Data

(60) Provisional application No. 62/180,963, filed on Jun. 17, 2015.

(51) Int. Cl.
*C07F 9/6561* (2006.01)
*C07C 57/15* (2006.01)

(52) U.S. Cl.
CPC .......... *C07F 9/65616* (2013.01); *C07C 57/15* (2013.01); *C07B 2200/13* (2013.01)

(58) Field of Classification Search
None
See application file for complete search history.

(56) References Cited

U.S. PATENT DOCUMENTS

| 8,754,065 | B2 * | 6/2014 | Liu | ...................... C07D 473/34 514/81 |
| 2005/0124583 | A1 | 6/2005 | Becker et al. | |

FOREIGN PATENT DOCUMENTS

| CN | 104558036 A | 4/2015 | |
| IN | WO 2015107451 A2 * | 7/2015 | .......... C07F 9/65616 |
| NL | EP 0903341 A1 * | 3/1999 | .......... C07C 323/36 |
| WO | WO-2013025788 A1 | 2/2013 | |
| WO | WO-2014195724 A1 | 12/2014 | |
| WO | WO-2015107451 A2 | 7/2015 | |
| WO | WO-2015176602 A1 | 11/2015 | |

OTHER PUBLICATIONS

International Search Report and Written Opinion for PCT/US2016/037268 Mailed Aug. 31, 2016.

* cited by examiner

*Primary Examiner* — Deepak Rao
*Assistant Examiner* — Laura Daniel
(74) *Attorney, Agent, or Firm* — Joel Silver

(57) ABSTRACT

The present invention relates to co-crystals, salts and crystalline forms of tenofovir alafenamide and methods for preparation, use and isolation of such compounds.

12 Claims, 26 Drawing Sheets

US 9,777,028 B2

CO-CRYSTALS, SALTS AND SOLID FORMS OF TENOFOVIR ALAFENAMIDE

CROSS-REFERENCES TO RELATED APPLICATIONS

This application claims priority to U.S. Provisional Application No. 62/180,963, filed Jun. 17, 2015, which is incorporated in its entirety herein for all purposes.

BACKGROUND OF THE INVENTION

Tenofovir alafenamide (TAF) is a nucleotide reverse transcriptase inhibitor useful for the treatment and prevention of HIV and HBV. TAF hemifumarate is described in U.S. Pat. No. 8,754,065 (incorporated by reference herein in its entirety). U.S. Pat. No. 6,043,230 (incorporated by reference herein in its entirety) and other publications describe the antiviral specificity of nucleotide analogs, such as tenofovir disoproxil.

SUMMARY OF THE INVENTION

The present disclosure provides co-crystals, salts and crystalline forms of tenofovir alafenamide and methods for the preparation, use and isolation of such forms.

Some embodiments provide tenofovir alafenamide sesquifumarate and crystal forms thereof. Some embodiments provide tenofovir alafenamide sesquifumarate solvates and crystal forms thereof wherein the solvent is selected from the group consisting of isopropanol, methyl ethyl ketone, tetrahydrofuran and acetone.

Another embodiment provides tenofovir alafenamide oxalate and crystal forms thereof. Another embodiment provides tenofovir alafenamide malonate and crystal forms thereof. Another embodiment provides tenofovir alafenamide L-malate and crystal forms thereof. Another embodiment provides tenofovir alafenamide saccharin and crystal forms thereof. Another embodiment provides tenofovir alafenamide mucate and crystal forms thereof. Another embodiment provides tenofovir alafenamide maleate and crystal forms thereof. Another embodiment provides tenofovir alafenamide hydrochloride and crystal forms thereof. Another embodiment provides tenofovir alafenamide ethanesulfonate and crystal forms thereof. Another embodiment provides tenofovir alafenamide benzenesulfonate and crystal forms thereof.

Another embodiment provides a crystal form of tenofovir alafenamide methanesulfonate, wherein the XRPD pattern comprises 2theta values of 8.7±0.2, 9.9±0.2, 10.1±0.2, and 19.7±0.2. Another embodiment provides a crystal form of tenofovir alafenamide methanesulfonate having an XRPD substantially as shown in FIG. 16a.

Another embodiment provides a crystal form of tenofovir alafenamide methanesulfonate, wherein the XRPD pattern comprises 2theta values of 9.0, 9.5, 18.6, and 22.4±0.2. Another embodiment provides a crystal form of tenofovir alafenamide methanesulfonate having an XRPD substantially as shown in FIG. 16b.

Another embodiment provides tenofovir alafenamide sulfate and crystal forms thereof.

In some embodiments, is provided a pharmaceutical composition comprising the co-crystals, salts and/or crystal forms of tenofovir alafenamide disclosed herein and a pharmaceutically acceptable excipient.

In some embodiments, is provided a method for treating an HIV infection comprising administering to a subject in need thereof a therapeutically effective amount of the co-crystals, salts and/or crystal forms of tenofovir alafenamide disclosed herein.

In some embodiments, is provided a method for treating a hepatitis B virus (HBV) infection comprising administering to a subject in need thereof a therapeutically effective amount of the co-crystals, salts and/or crystal forms of tenofovir alafenamide disclosed herein.

In some embodiments, are provided co-crystals, salts and/or crystal forms of tenofovir alafenamide disclosed herein or a composition thereof, for use in the prophylactic or therapeutic treatment of HIV.

In some embodiments, are provided co-crystals, salts and/or crystal forms of tenofovir alafenamide disclosed herein or a composition thereof, for use in the prophylactic or therapeutic treatment of HBV.

DETAILED DESCRIPTION OF THE INVENTION

Definitions

Figure 1:
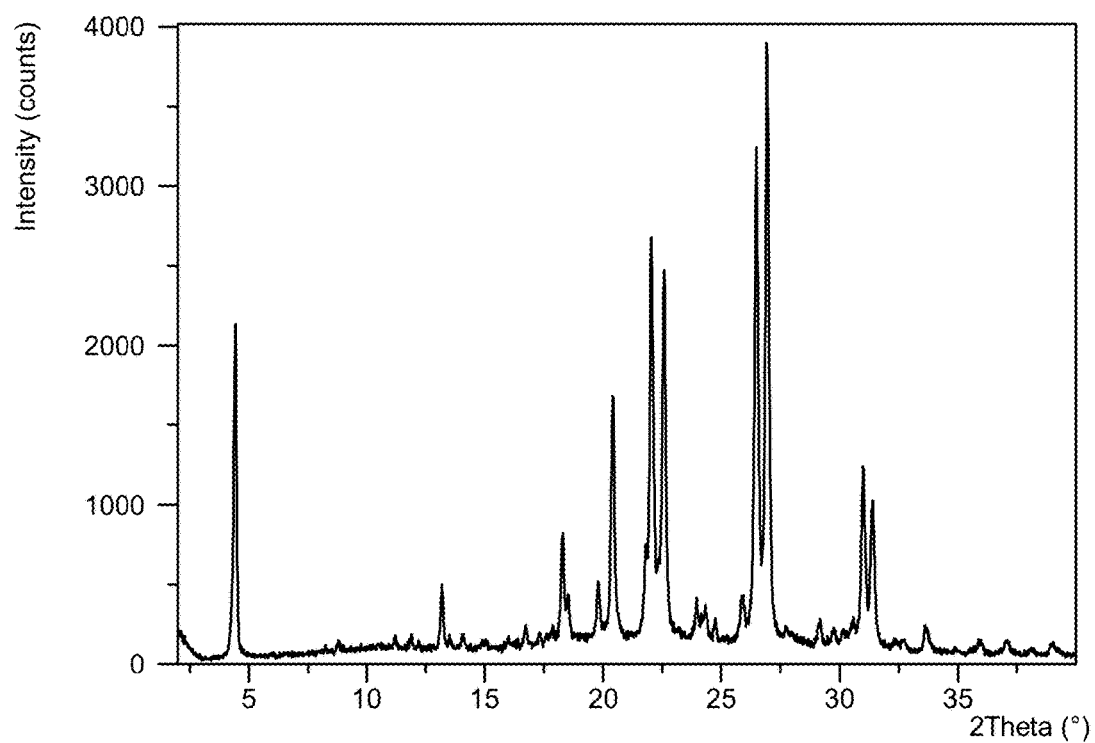
FIG. 1. Presented in FIG. 1 is the experimental X-ray powder diffraction (XRPD) pattern of TAF sesquifumarate isopropanol solvate FIG. 2. Presented in FIG. 2 is the experimental X-ray powder diffraction (XRPD) pattern of TAF sesquifumarate methyl ethyl ketone solvate FIG. 3. Presented in FIG. 3 is the experimental X-ray powder diffraction (XRPD) pattern of TAF sesquifumarate THF solvate FIG. 4. Presented in FIG. 4 is the experimental X-ray powder diffraction (XRPD) pattern of TAF sesquifumarate acetone solvate FIG. 5. Presented in FIG. 5 is the Experimental X-ray powder diffraction (XRPD) pattern of TAF sesquifumarate FIG. 6. Presented in FIG. 6 is the experimental X-ray powder diffraction (XRPD) pattern of TAF oxalate FIG. 7. Presented in FIG. 7 is the Experimental X-ray powder diffraction (XRPD) pattern of TAF malonate FIG. 8. Presented in FIG. 8 is the experimental X-ray powder diffraction (XRPD) pattern of TAF L-malate FIG. 9. Presented in FIG. 9 is the experimental X-ray powder diffraction (XRPD) pattern of TAF saccharin FIG. 10. Presented in FIG. 10 is the experimental X-ray powder diffraction (XRPD) pattern of TAF mucate pattern 1

The term "crystallizing" refers to the process of formation of a crystalline form from an amorphous form or from a discrete crystal form (i.e. interconversion of crystalline forms).

"DSC" means differential scanning calorimetry.
"MEK" means methyl ethyl ketone.
"IPA" means isopropanol.
"MTBE" means methyl tert-butyl ether.
"EtOAc" means ethyl acetate.
"THF" means tetrahydrofuran.
"RH" means relative humidity.
"X Volume" when used to refer to a quantity of solvent used in a reaction means that X volumes of solvent are used for each unit weight of tenofovir alafenamide. For example, "50 volumes" of solvent refers to 50 mL of solvent for 1 g of tenofovir alafenamide or 50 L of solvent for 1 kg of tenofovir alafenamide.

"Solvate" refers to an aggregate that comprises one or more molecules of a compound described herein with one or more molecules of solvent. The solvent may be water, in which case the solvate may be a hydrate. Alternatively, the solvent may be an organic solvent.

When referring to a composition comprising a unique pattern, the term "material" refers to a singular form or mixture of crystalline and/or amorphous forms.

"PXRD" or "XRPD" used interchangeably refer to the X-ray powder diffraction pattern of a solid form.

The term "substantially" in reference to an X-ray powder diffraction pattern refers to a spectrum having at least 4, 5, 6, 7, 8, 9, 10, 11, 12, 13, 14 or 15 peaks in common with the referenced pattern; or a pattern having peaks at ±0.2 degree of two theta angle within the referenced peaks.

"Tenofovir Alafenamide" or "TAF" has the following chemical structure:

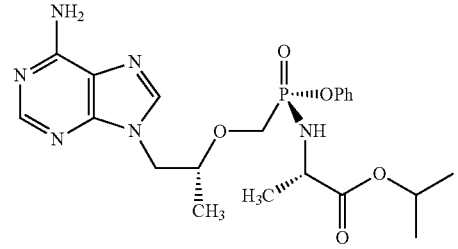 [SMILES: CC(C)OC(=O)[C@H](C)N[P@](=O)(CO[C@H](C)Cn1cnc2c(N)ncnc21)Oc1ccccc1]

Seeding is a technique of using a single crystal or more to induce the formation of more crystals from a mixture, solution, or suspension. A seeding amount is the amount of material that, when added to a mixture, solution, or suspension, is able to cause the formation of the desired form of a compound. While in theory, this amount can be very small, in practice, a larger amount is used. This amount can be any amount that can be reasonably handled and is sufficient to cause the formation of the desired form of a compound. As a non-limiting example, amounts of 0.0001% to 50% wt/wt of the seeding compound based on a reference compound can be used as a seeding amount.

The term "C" when used in reference to temperature means centigrade or Celsius.

"Ambient temperature" or "room temperature" is the air temperature surrounding an object. It is the temperature inside a room, which generally is from about 15 to about 25 degrees centigrade.

"Therapeutically effective amount" refers to that amount of the compound being administered which will prevent a condition, or will relieve to some extent one or more of the symptoms of the disorder being treated. Pharmaceutical compositions suitable for use herein include compositions wherein the active ingredients are contained in an amount sufficient to achieve the intended purpose. Determination of a therapeutically effective amount is well within the capability of those skilled in the art, especially in light of the detailed disclosure provided herein.

In practice, the amount of the compound to be administered ranges from about 0.001 to 100 mg per kg of body weight, such total dose being given at one time or in divided doses. It may be administered alone or in combination with one or more other drugs. Generally, it will be administered as a formulation in association with one or more pharmaceutically acceptable excipients. The choice of excipient will to a large extent depend on factors such as the particular mode of administration, the effect of the excipient on solubility and stability, and the nature of the dosage form.

Pharmaceutical compositions suitable for the delivery of compounds described herein and methods for their preparation will be readily apparent to those skilled in the art. Such compositions and methods for their preparation may be found, for example, in *Remington's Pharmaceutical Sciences,* 19th Edition (Mack Publishing Company, 1995).

In one embodiment, the present invention provides tenofovir alafenamide sesquifumarate.

In some embodiments, the ratio of fumaric acid to tenofovir alafenamide is 1.5±0.1.

In some embodiments, the ratio of fumaric acid to tenofovir alafenamide is 1.5±0.2.

In some embodiments, the ratio of fumaric acid to tenofovir alafenamide is 1.5±0.3.

In some embodiments, the ratio of fumaric acid to tenofovir alafenamide is 1.5±0.4.

In some embodiments, the ratio of fumaric acid to tenofovir alafenamide is 1.5±0.05.

In some embodiments, tenofovir alafenamide sesquifumarate is a solvate wherein the solvent is selected from the group consisting of isopropanol, methyl ethyl ketone, tetrahydrofuran and acetone.

In some embodiments, tenofovir alafenamide sesquifumarate is a solvate wherein the solvent is isopropanol.

Another embodiment provides a crystal form of tenofovir alafenamide sesquifumarate solvate wherein the solvent is isopropanol and the XRPD pattern comprises 2theta values of 4.5±0.2, 20.4±0.2, 26.5±0.2, and 26.9±0.2.

Another embodiment provides a crystal form of tenofovir alafenamide sesquifumarate solvate wherein the solvent is isopropanol and the XRPD pattern comprises 2theta values selected from the group consisting of at least 4, 5, 6, 7, 8, 9, 10, 11, 12, 13, 14, 15, 16, 17, 18, 19, 20, 21, 22, 23, or 24 of the following: 4.5, 11.8, 13.2, 14.1, 16.7, 18.3, 19.8, 20.4, 22.0, 22.6, 23.9, 24.3, 25.9, 26.5, 26.9, 29.1, 29.7, 31.0, 31.4, 32.6, 33.6, 35.9, 37.1, and 39.0.

Another embodiment provides a crystal form of tenofovir alafenamide sesquifumarate solvate wherein the solvent is isopropanol and the XRPD is substantially as shown in FIG. 1.

Another embodiment provides a crystal form of tenofovir alafenamide sesquifumarate solvate wherein the solvent is isopropanol and the differential scanning calorimetry (DSC) has onset endotherms of 54±2° C. and 112±2° C.

Another embodiment provides a crystal form of tenofovir alafenamide sesquifumarate solvate wherein the solvent is isopropanol and the differential scanning calorimetry (DSC) has onset endotherms of 54±1° C. and 112±1° C.

Another embodiment provides a crystal form of tenofovir alafenamide sesquifumarate solvate wherein the solvent is isopropanol and the differential scanning calorimetry (DSC) has onset endotherms of about 54° C. and about 112° C.

In some embodiments, tenofovir alafenamide sesquifumarate is a solvate wherein the solvent is methyl ethyl ketone.

Another embodiment provides a crystal form of tenofovir alafenamide sesquifumarate solvate wherein the solvent is methyl ethyl ketone and the XRPD pattern comprises 2theta values of 4.6±0.2, 22.8±0.2, 27.4±0.2, and 27.8±0.2.

Another embodiment provides a crystal form of tenofovir alafenamide sesquifumarate solvate wherein the solvent is methyl ethyl ketone and the XRPD pattern comprises 2theta values selected from the group consisting of at least 4, 5, 6, 7, 8, 9, 10, 11, 12, 13, 14, 15, 16, 17, 18, 19, 20, 21, 22, 23, 24, 25, 26, 27, 28, 29 or 30 of the following: 4.6, 10.6, 11.3, 11.9, 12.4, 13.6, 15.0, 15.3, 16.2, 17.1, 17.6, 18.2, 18.7, 19.1, 19.5, 20.4, 20.7, 21.1, 22.4, 22.8, 23.3, 24.5, 27.4, 27.8, 30.1, 32.0, 32.4, 33.6, 34.8, and 37.0.

Figure 2:
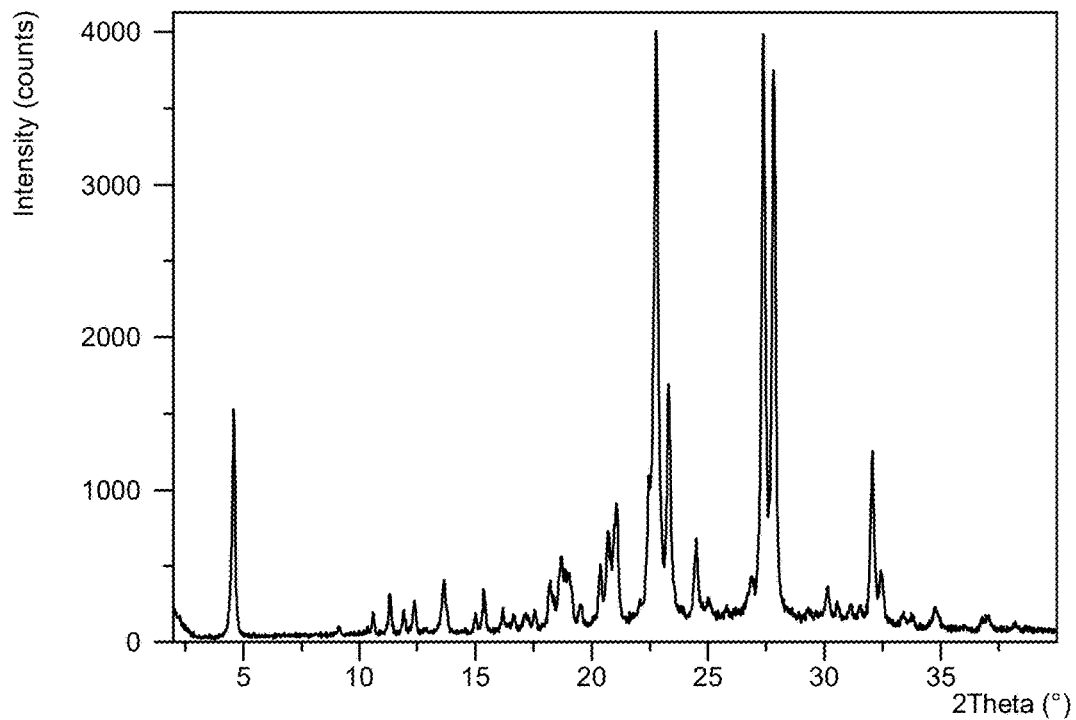

Another embodiment provides a crystal form of tenofovir alafenamide sesquifumarate solvate wherein the solvent is methyl ethyl ketone and the XRPD is substantially as shown in FIG. 2.

In some embodiments, tenofovir alafenamide sesquifumarate is a solvate wherein the solvent is tetrahydrofuran.

Another embodiment provides a crystal form of tenofovir alafenamide sesquifumarate solvate wherein the solvent is tetrahydrofuran and the XRPD pattern comprises 2theta values of 4.5±0.2, 22.6±0.2, 27.2±0.2, and 27.7±0.2.

Another embodiment provides a crystal form of tenofovir alafenamide sesquifumarate solvate wherein the solvent is tetrahydrofuran and the XRPD pattern comprises 2theta values selected from the group consisting of at least 4, 5, 6, 7, 8, 9, 10, 11, 12, 13, 14, 15, 16, 17, 18, 19, 20, 21, 22, or 23 of the following: 4.5, 10.5, 11.2, 11.9, 12.3, 13.5, 15.3, 16.3, 18.2, 18.6, 20.2, 20.9, 22.6, 23.1, 24.4, 27.2, 27.7, 29.9, 30.9, 31.8, 34.6, 36.7, and 38.0.

Figure 3:
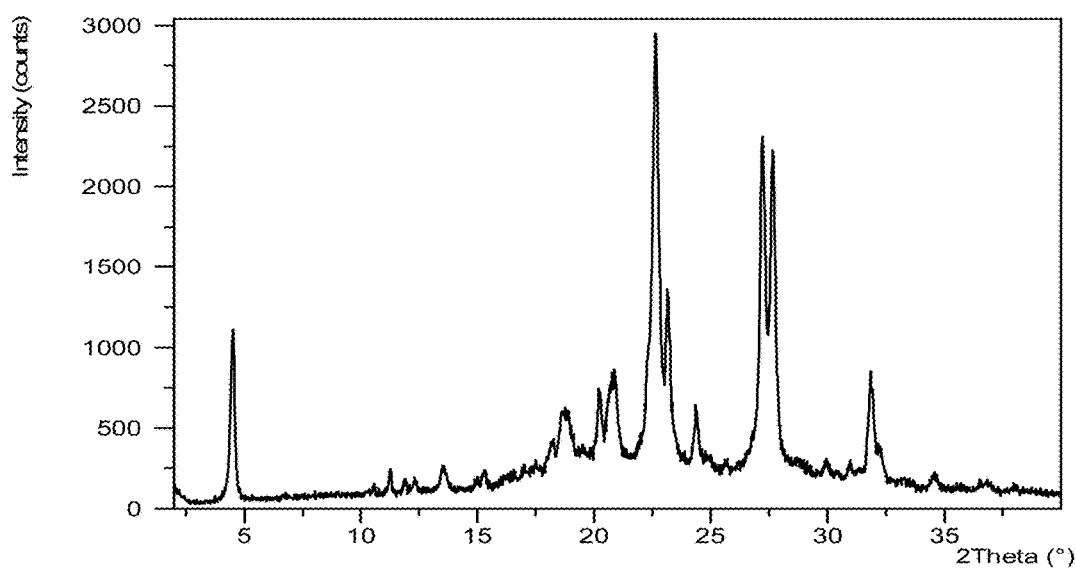

Another embodiment provides a crystal form of tenofovir alafenamide sesquifumarate solvate wherein the solvent is tetrahydrofuran and the XRPD is substantially as shown in FIG. 3.

In some embodiments, tenofovir alafenamide sesquifumarate is a solvate wherein the solvent is acetone.

Another embodiment provides a crystal form of tenofovir alafenamide sesquifumarate solvate wherein the solvent is acetone and the XRPD pattern comprises 2theta values of 4.6±0.2, 22.9±0.2, 27.6±0.2 and 28.0±0.2.

Another embodiment provides a crystal form of tenofovir alafenamide sesquifumarate solvate wherein the solvent is acetone and the XRPD pattern comprises 2theta values selected from the group consisting of at least 4, 5, 6, 7, 8, 9, 10, 11, 12, 13, 14, 15, 16, 17, 18, 19, 20, or 21 of the following: 4.6, 10.5, 11.3, 12.4, 13.7, 15.4, 17.2, 17.6, 18.3, 19.1, 20.5, 20.8, 21.2, 22.5, 22.9, 23.5, 24.6, 27.6, 28.0, 30.3, and 32.3.

Figure 4:
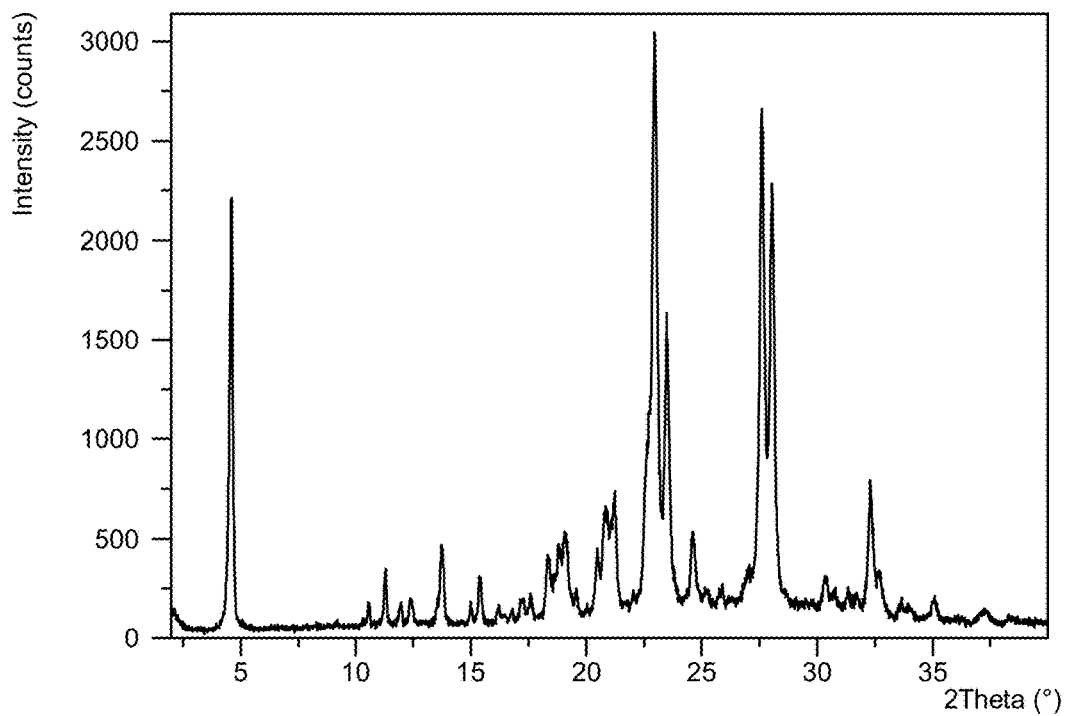

Another embodiment provides a crystal form of tenofovir alafenamide sesquifumarate solvate wherein the solvent is acetone and the XRPD is substantially as shown in FIG. 4.

Another embodiment provides a crystal form of tenofovir alafenamide sesquifumarate, wherein the XRPD pattern comprises 2theta values of 5.0±0.2, 20.1±0.2, 22.7±0.2, and 25.2±0.2.

Another embodiment provides a crystal form of tenofovir alafenamide sesquifumarate, wherein the XRPD pattern comprises 2theta values selected from the group consisting of at least 4, 5, 6, 7, 8, 9, 10, 11, 12, 13, 14, 15, or 16 of the following: 5.0, 10.6, 11.0, 15.0, 16.2, 17.9, 18.8, 20.1, 22.7, 24.5, 25.2, 27.7, 28.9, 29.4, 30.3, and 32.9.

Figure 5:
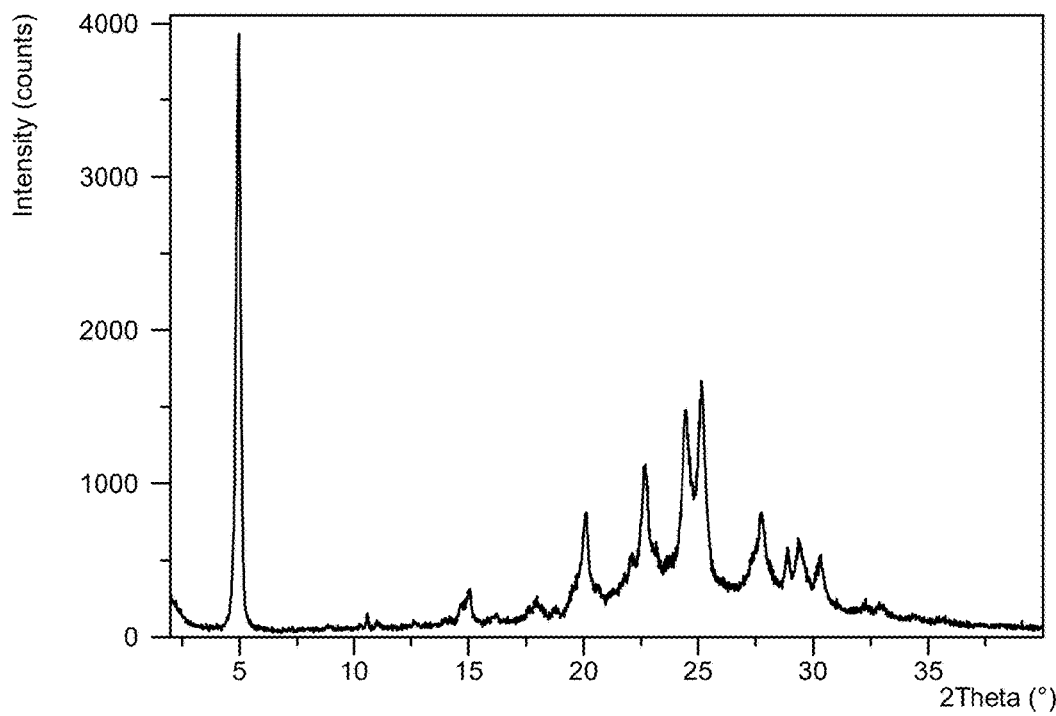

Another embodiment provides a crystal form of tenofovir alafenamide sesquifumarate, having an XRPD substantially as shown in FIG. 5.

Another embodiment provides a crystal form of tenofovir alafenamide sesquifumarate, having differential scanning calorimetry (DSC) onset endotherms of 110±2° C. and 118±2° C.

Another embodiment provides a crystal form of tenofovir alafenamide sesquifumarate, having differential scanning calorimetry (DSC) onset endotherms of 110±1° C. and 118±1° C.

Another embodiment provides a crystal form of tenofovir alafenamide sesquifumarate, having differential scanning calorimetry (DSC) onset endotherms of about 110° C. and about 118° C.

Another embodiment provides tenofovir alafenamide oxalate.

In some embodiments, the ratio of oxalic acid to tenofovir alafenamide is 1±0.5.

In some embodiments, the ratio of oxalic acid to tenofovir alafenamide is 1±0.4.

In some embodiments, the ratio of oxalic acid to tenofovir alafenamide is 1±0.3.

In some embodiments, the ratio of oxalic acid to tenofovir alafenamide is 1±0.2.

In some embodiments, the ratio of oxalic acid to tenofovir alafenamide is 1±0.1.

In some embodiments, the ratio of oxalic acid to tenofovir alafenamide is 1±0.05.

Another embodiment provides a crystal form of tenofovir alafenamide oxalate wherein the XRPD pattern comprises 2theta values of 4.1±0.2, 9.7±0.2, 20.8±0.2, and 25.0±0.2.

Another embodiment provides a crystal form of tenofovir alafenamide oxalate wherein the XRPD pattern comprises 2theta values selected from the group consisting of at least 4, 5, 6, 7, 8, 9, 10, or 11 of the following: 4.1, 7.6, 9.7, 12.4, 12.8, 16.6, 20.8, 22.8, 24.0, 25.0, and 29.1.

Figure 6:
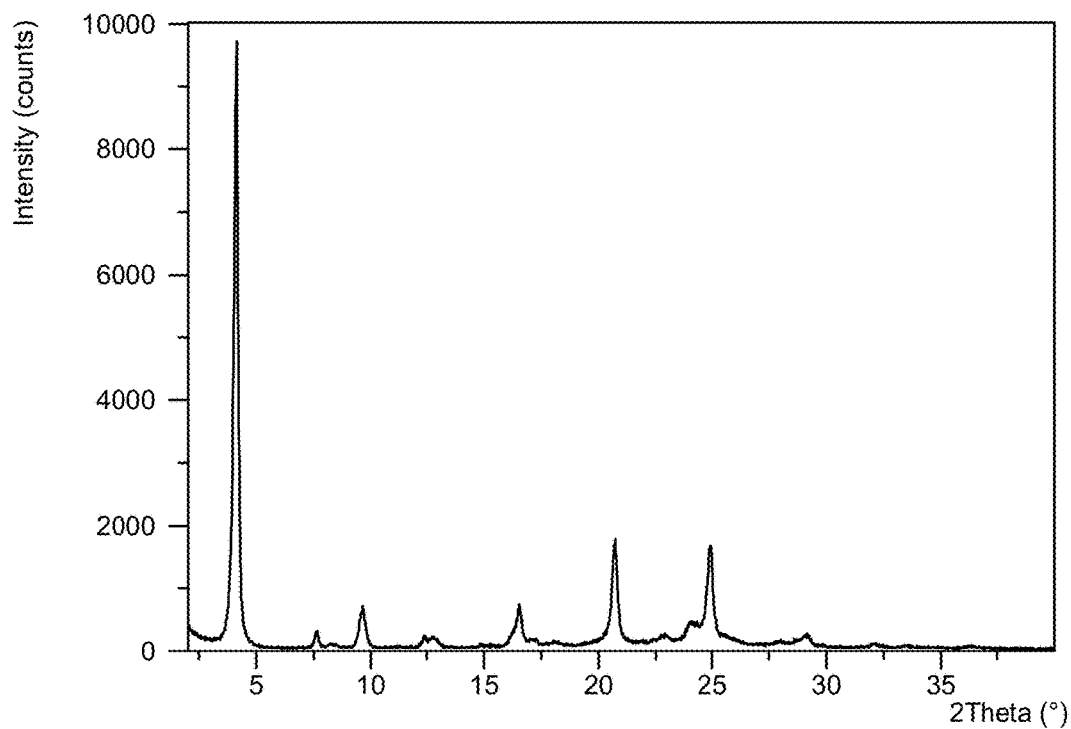

Another embodiment provides a crystal form of tenofovir alafenamide oxalate having an XRPD substantially as shown in FIG. 6.

Another embodiment provides a crystal form of tenofovir alafenamide oxalate having a differential scanning calorimetry (DSC) onset endotherm of 196±2° C.

Another embodiment provides a crystal form of tenofovir alafenamide oxalate having a differential scanning calorimetry (DSC) onset endotherm of 196±1° C.

Another embodiment provides a crystal form of tenofovir alafenamide oxalate having a differential scanning calorimetry (DSC) onset endotherm of about 196° C.

Another embodiment provides tenofovir alafenamide malonate.

In some embodiments, the ratio of malonic acid to tenofovir alafenamide is 1±0.5.

In some embodiments, the ratio of malonic acid to tenofovir alafenamide is 1±0.4.

In some embodiments, the ratio of malonic acid to tenofovir alafenamide is 1±0.3.

In some embodiments, the ratio of malonic acid to tenofovir alafenamide is 1±0.2.

In some embodiments, the ratio of malonic acid to tenofovir alafenamide is 1±0.1.

In some embodiments, the ratio of malonic acid to tenofovir alafenamide is 1±0.05.

Another embodiment provides a crystal form of tenofovir alafenamide malonate, wherein the XRPD pattern comprises 2theta values of 6.9±0.2, 8.7±0.2, 15.3±0.2, and 20.1±0.2.

Another embodiment provides a crystal form of tenofovir alafenamide malonate, wherein the XRPD pattern comprises 2theta values selected from the group consisting of at least 4, 5, 6, 7, 8, 9, 10, 11, 12, 13, 14, 15, 16, 17, 18, 19, 20, 21, or 22 of the following: 4.0, 6.9, 8.7, 11.8, 12.9, 15.0, 15.3, 17.4, 18.2, 19.4, 20.1, 20.5, 21.2, 21.9, 22.9, 24.1, 25.6, 26.4, 27.0, 27.7, 29.0, and 29.7.

Figure 7:
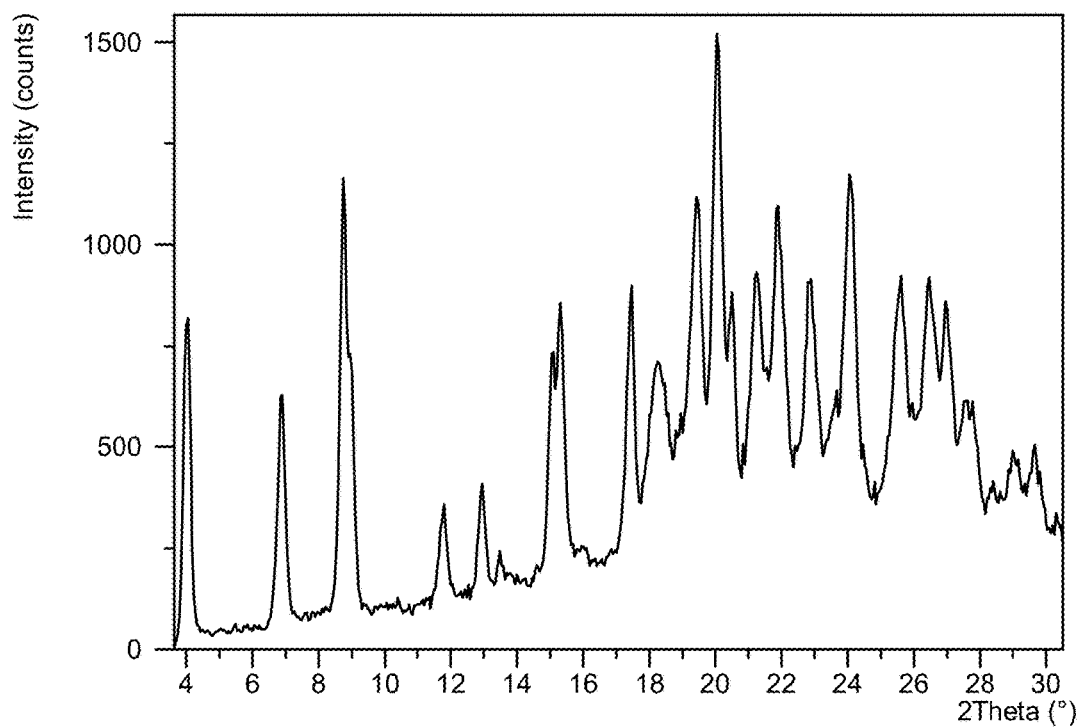

Another embodiment provides a crystal form of tenofovir alafenamide malonate having an XRPD substantially as shown in FIG. 7.

Another embodiment provides a crystal form of tenofovir alafenamide malonate having a differential scanning calorimetry (DSC) onset endotherm of 120±2° C.

Another embodiment provides a crystal form of tenofovir alafenamide malonate having a differential scanning calorimetry (DSC) onset endotherm of 120±1° C.

Another embodiment provides a crystal form of tenofovir alafenamide malonate having a differential scanning calorimetry (DSC) onset endotherm of about 120° C.

Another embodiment provides tenofovir alafenamide L-malate.

In some embodiments, the ratio of L-malic acid to tenofovir alafenamide is 1±0.5.

In some embodiments, the ratio of L-malic acid to tenofovir alafenamide is 1±0.4.

In some embodiments, the ratio of L-malic acid to tenofovir alafenamide is 1±0.3.

In some embodiments, the ratio of L-malic acid to tenofovir alafenamide is 1±0.2.

In some embodiments, the ratio of L-malic acid to tenofovir alafenamide is 1±0.1.

In some embodiments, the ratio of L-malic acid to tenofovir alafenamide is 1±0.05.

Another embodiment provides a crystal form of tenofovir alafenamide L-malate wherein the XRPD pattern comprises 2theta values of 10.0±0.2, 13.9±0.2, 16.5±0.2, and 21.2±0.2.

Another embodiment provides a crystal form of tenofovir alafenamide L-malate wherein the XRPD pattern comprises 2theta values selected from the group consisting of at least 4, 5, 6, 7, 8, 9, 10, 11, 12, 13, 14, 15, or 16 of the following: 5.3, 10.0, 12.0, 13.4, 13.9, 15.3, 16.5, 17.9, 19.4, 20.2, 21.2, 22.0, 23.1, 24.0, 26.2, and 27.0.

Figure 8:
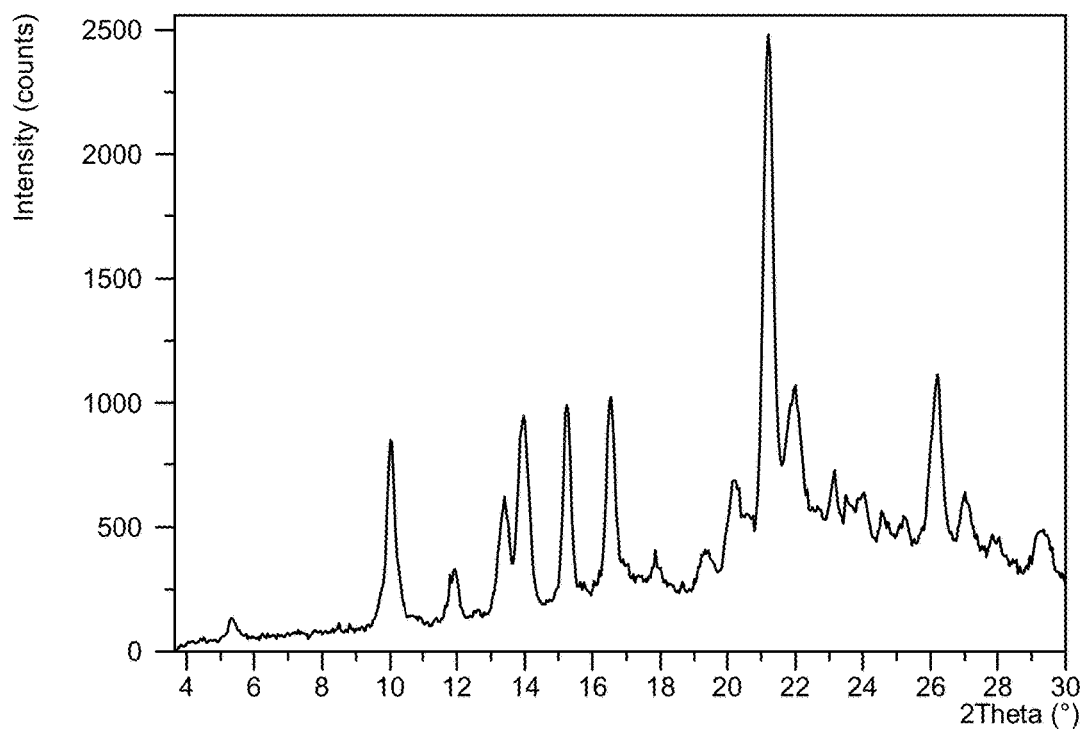

Another embodiment provides a crystal form of tenofovir alafenamide L-malate having an XRPD substantially as shown in FIG. 8.

Another embodiment provides a crystal form of tenofovir alafenamide L-malate having a differential scanning calorimetry (DSC) onset endotherm of 111±2° C.

Another embodiment provides a crystal form of tenofovir alafenamide L-malate having a differential scanning calorimetry (DSC) onset endotherm of 111±1° C.

Another embodiment provides a crystal form of tenofovir alafenamide L-malate having a differential scanning calorimetry (DSC) onset endotherm of about 111° C.

Another embodiment provides tenofovir alafenamide saccharin.

In some embodiments, the ratio of saccharin to tenofovir alafenamide is 1±0.5.

In some embodiments, the ratio of saccharin to tenofovir alafenamide is 1±0.4.

In some embodiments, the ratio of saccharin to tenofovir alafenamide is 1±0.3.

In some embodiments, the ratio of saccharin to tenofovir alafenamide is 1±0.2.

In some embodiments, the ratio of saccharin to tenofovir alafenamide is 1±0.1.

In some embodiments, the ratio of saccharin to tenofovir alafenamide is 1±0.05.

Another embodiment provides a crystal form of tenofovir alafenamide saccharin, wherein the XRPD pattern comprises 2theta values of 7.3±0.2, 14.4±0.2, 16.0±0.2, and 18.6±0.2.

Another embodiment provides a crystal form of tenofovir alafenamide saccharin, wherein the XRPD pattern comprises 2theta values selected from the group consisting of at least 4, 5, 6, 7, 8, 9, 10, 11, 12, 13, 14, 15, 16, 17, 18, or 19 of the following: 3.7, 7.3, 7.8, 9.9, 10.8, 11.3, 12.3, 13.8, 14.4, 16.0, 18.0, 18.6, 21.7, 22.5, 23.7, 25.0, 26.3, 27.7, and 29.2.

Figure 9:
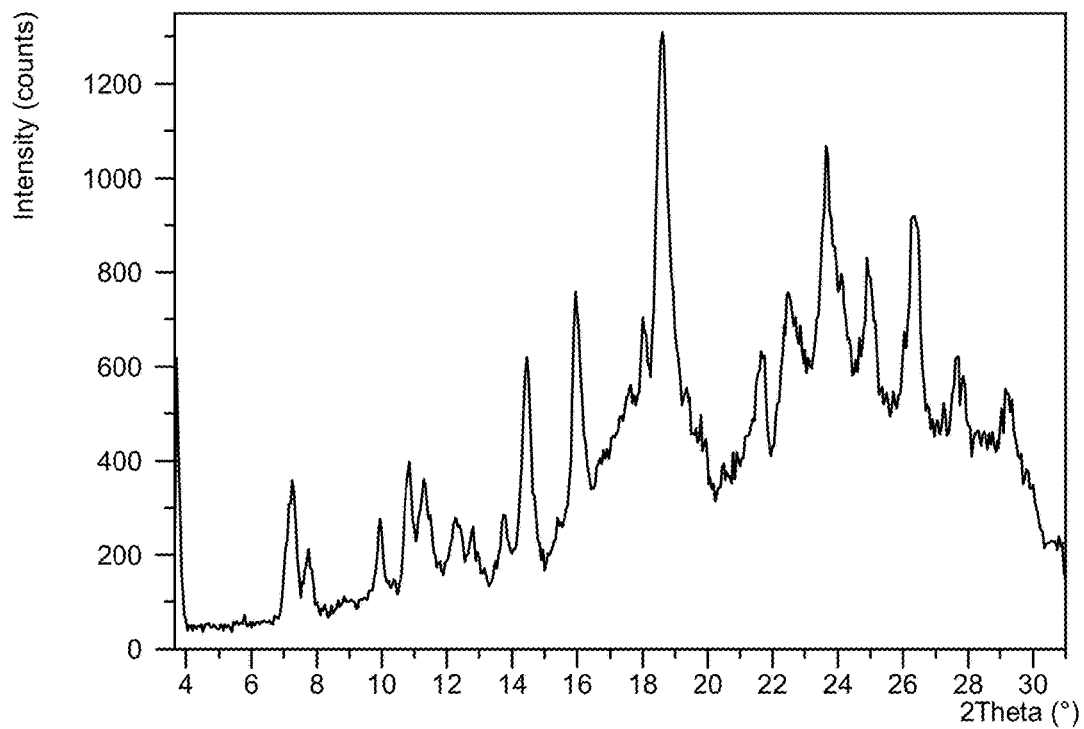

Another embodiment provides a crystal form of tenofovir alafenamide saccharin having an XRPD substantially as shown in FIG. 9.

Another embodiment provides a crystal form of tenofovir alafenamide saccharin having a differential scanning calorimetry (DSC) onset endotherm of 125±2° C.

Another embodiment provides a crystal form of tenofovir alafenamide saccharin having a differential scanning calorimetry (DSC) onset endotherm of 125±1° C.

Another embodiment provides a crystal form of tenofovir alafenamide saccharin having a differential scanning calorimetry (DSC) onset endotherm of about 125° C.

Another embodiment provides tenofovir alafenamide mucate.

In some embodiments, the ratio of mucic acid to tenofovir alafenamide is 2±0.5.

In some embodiments, the ratio of mucic acid to tenofovir alafenamide is 2±0.4.

In some embodiments, the ratio of mucic acid to tenofovir alafenamide is 2±0.3.

In some embodiments, the ratio of mucic acid to tenofovir alafenamide is 2±0.2.

In some embodiments, the ratio of mucic acid to tenofovir alafenamide is 2±0.1.

In some embodiments, the ratio of mucic acid to tenofovir alafenamide is 2±0.05.

Another embodiment provides a crystal form of tenofovir alafenamide mucate wherein the XRPD pattern comprises 2theta values of 6.4±0.2, 7.2±0.2, 18.1±0.2, and 19.5±0.2.

Another embodiment provides a crystal form of tenofovir alafenamide mucate wherein the XRPD pattern comprises 2theta values selected from the group consisting of at least 4, 5, 6, 7, 8, 9, 10, 11, 12, or 13 of the following: 3.8, 4.3, 6.4, 7.2, 8.4, 10.6, 11.7, 12.8, 18.1, 19.5, 21.0, 22.9, and 26.9.

Figure 10:
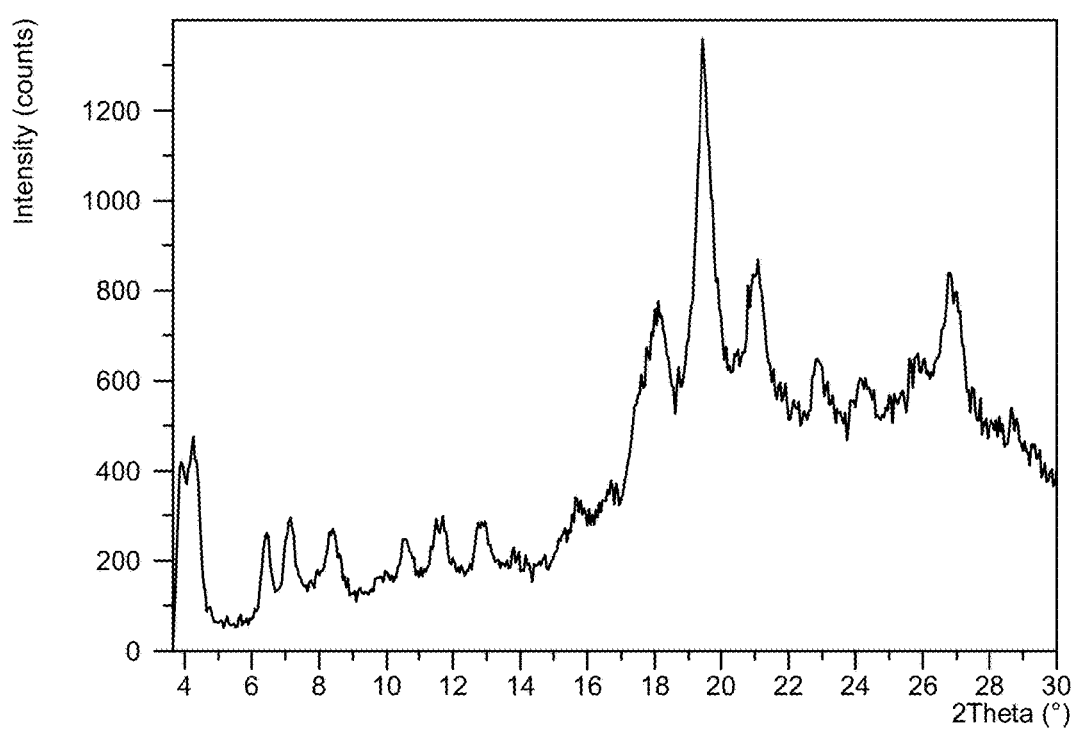

Another embodiment provides a crystal form of tenofovir alafenamide mucate having an XRPD substantially as shown in FIG. 10.

Another embodiment provides a crystal form of tenofovir alafenamide mucate having a differential scanning calorimetry (DSC) onset endotherm of 180±2° C.

Another embodiment provides a crystal form of tenofovir alafenamide mucate having a differential scanning calorimetry (DSC) onset endotherm of 180±1° C.

Another embodiment provides a crystal form of tenofovir alafenamide mucate having a differential scanning calorimetry (DSC) onset endotherm of about 180° C.

Another embodiment provides a crystal form of tenofovir alafenamide mucate wherein the XRPD pattern comprises 2theta values of 8.5±0.2, 9.9±0.2, 16.9±0.2, and 21.1±0.2.

Another embodiment provides a crystal form of tenofovir alafenamide mucate wherein the XRPD pattern comprises 2theta values selected from the group consisting of at least 4, 5, 6, 7, 8, 9, 10, 11, or 12 of the following: 4.2, 6.7, 8.5, 9.9, 13.3, 16.9, 18.6, 19.6, 21.1, 22.9, 26.2, and 29.2.

Figure 11:
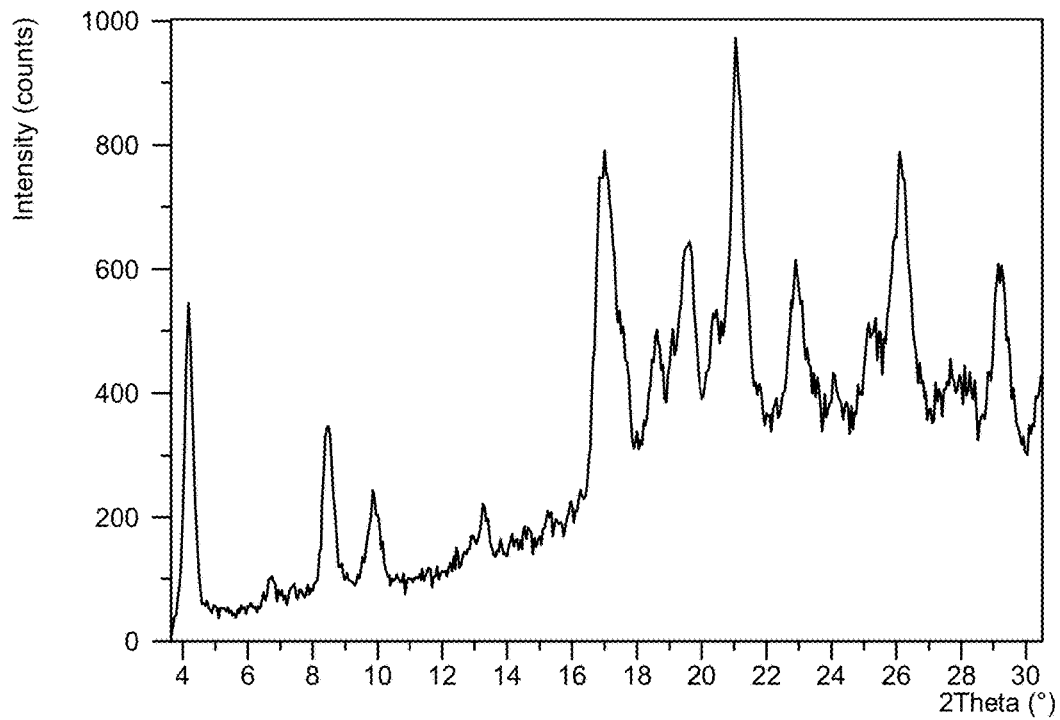
FIG. 11. Presented in FIG. 11 is the experimental X-ray powder diffraction (XRPD) pattern of TAF mucate pattern 2

Another embodiment provides a crystal form of tenofovir alafenamide mucate having an XRPD substantially as shown in FIG. 11.

Another embodiment provides a crystal form of tenofovir alafenamide mucate having a differential scanning calorimetry (DSC) onset endotherm of 179±2° C.

Another embodiment provides a crystal form of tenofovir alafenamide mucate having a differential scanning calorimetry (DSC) onset endotherm of 179±1° C.

Another embodiment provides a crystal form of tenofovir alafenamide mucate having a differential scanning calorimetry (DSC) onset endotherm of about 179° C.

Another embodiment provides tenofovir alafenamide maleate.

In some embodiments, the ratio of maleic acid to tenofovir alafenamide is 1±0.5.

In some embodiments, the ratio of maleic acid to tenofovir alafenamide is 1±0.4.

In some embodiments, the ratio of maleic acid to tenofovir alafenamide is 1±0.3.

In some embodiments, the ratio of maleic acid to tenofovir alafenamide is 1±0.2.

In some embodiments, the ratio of maleic acid to tenofovir alafenamide is 1±0.1.

In some embodiments, the ratio of maleic acid to tenofovir alafenamide is 1±0.05.

Another embodiment provides a crystal form of tenofovir alafenamide maleate wherein the XRPD pattern comprises 2theta values of 7.6±0.2, 18.1±0.2, 21.1±0.2, and 26.0±0.2.

Another embodiment provides a crystal form of tenofovir alafenamide maleate wherein the XRPD pattern comprises 2theta values selected from the group consisting of at least 4, 5, 6, 7, 8, 9, or 10 of the following: 4.2, 6.4, 7.6, 10.5, 12.6, 15.2, 18.1, 21.1, 24.4, and 26.0.

Figure 12:
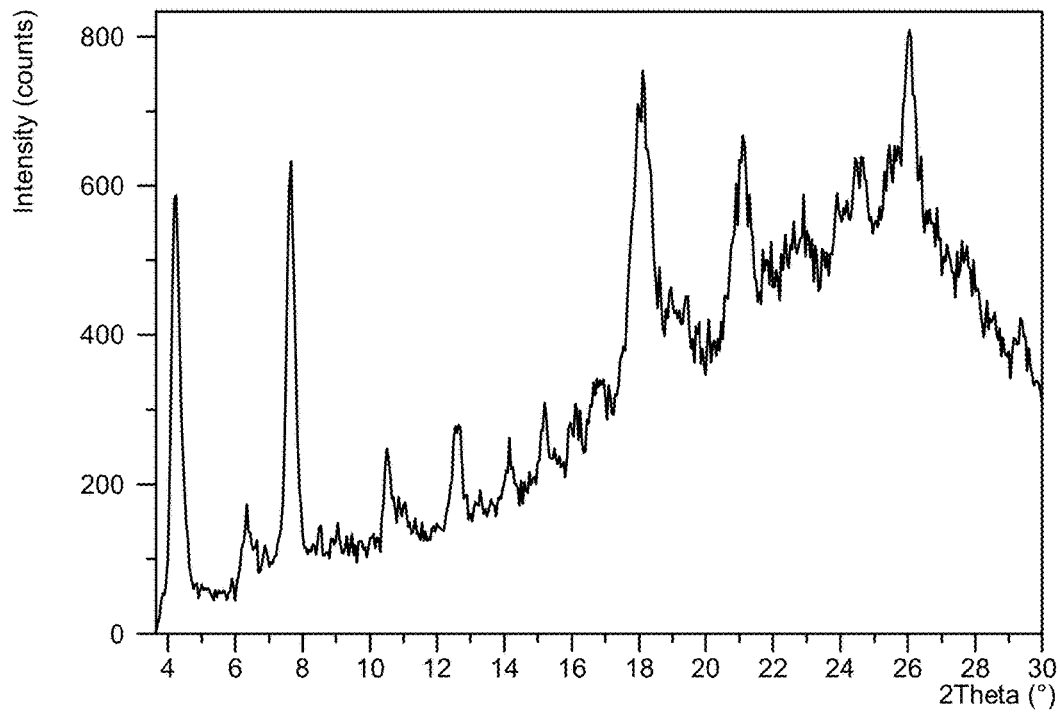
FIG. 12. Presented in FIG. 12 is the experimental X-ray powder diffraction (XRPD) pattern of TAF maleate FIG. 13. Presented in FIG. 13 is the experimental X-ray powder diffraction (XRPD) pattern of TAF hydrochloride FIG. 14. Presented in FIG. 14 is the experimental X-ray powder diffraction (XRPD) pattern of TAF ethanesulfonate FIG. 15. Presented in FIG. 15 is the experimental X-ray powder diffraction (XRPD) pattern of TAF benzenesulfonate FIG. 16a. Presented in FIG. 16a is the experimental X-ray powder diffraction (XRPD) pattern of TAF methanesulfonate pattern 1

Another embodiment provides a crystal form of tenofovir alafenamide maleate having an XRPD substantially as shown in FIG. 12.

Another embodiment provides a crystal form of tenofovir alafenamide maleate having a differential scanning calorimetry (DSC) onset endotherm of 114±2° C.

Another embodiment provides a crystal form of tenofovir alafenamide maleate having a differential scanning calorimetry (DSC) onset endotherm of 114±1° C.

Another embodiment provides a crystal form of tenofovir alafenamide maleate having a differential scanning calorimetry (DSC) onset endotherm of about 114° C.

Another embodiment provides tenofovir alafenamide hydrochloride.

In some embodiments, the ratio of hydrochloric acid to tenofovir alafenamide is 1±0.5.

In some embodiments, the ratio of hydrochloric acid to tenofovir alafenamide is 1±0.4.

In some embodiments, the ratio of hydrochloric acid to tenofovir alafenamide is 1±0.3.

In some embodiments, the ratio of hydrochloric acid to tenofovir alafenamide is 1±0.2.

In some embodiments, the ratio of hydrochloric acid to tenofovir alafenamide is 1±0.1.

In some embodiments, the ratio of hydrochloric acid to tenofovir alafenamide is 1±0.05.

Another embodiment provides a crystal form of tenofovir alafenamide hydrochloride wherein the XRPD pattern comprises 2theta values of 7.0±0.2, 8.6±0.2, 10.4±0.2, and 18.2±0.2.

Another embodiment provides a crystal form of tenofovir alafenamide hydrochloride wherein the XRPD pattern comprises 2theta values selected from the group consisting of at least 4, 5, 6, 7, 8, 9, 10, 11, 12, 13, 14, 15, 16, 17, or 18 of the following: 7.0, 8.6, 9.1, 10.4, 12.1, 13.4, 13.9, 14.8, 16.3, 18.2, 18.9, 20.9, 22.0, 24.2, 25.2, 26.6, 27.7, and 29.2.

Figure 13:
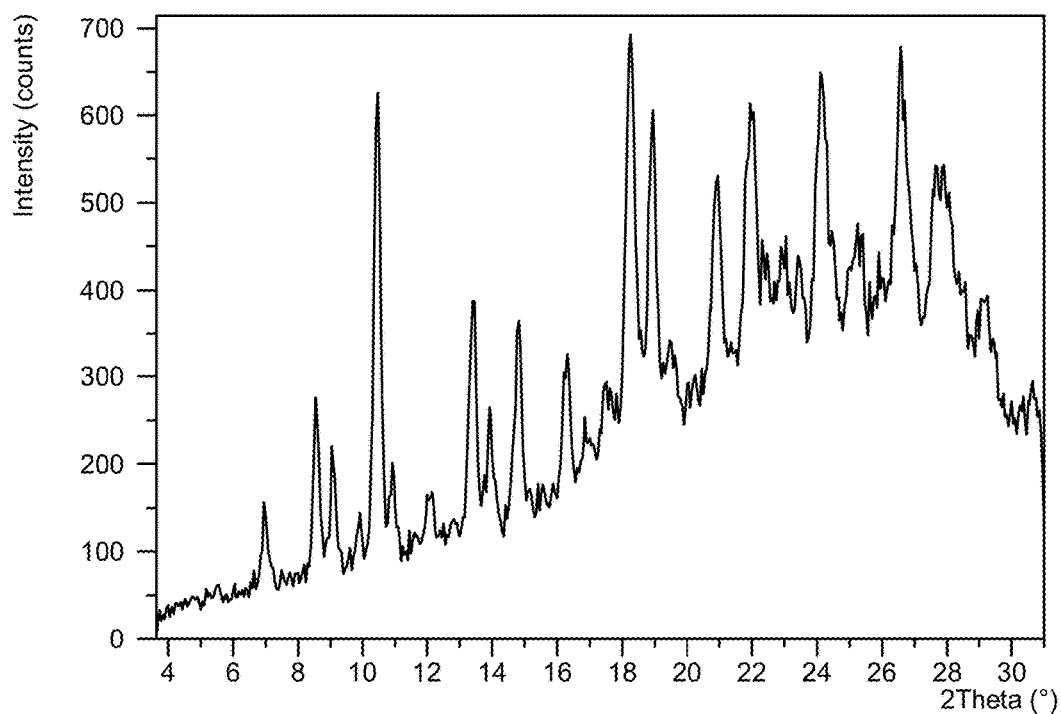

Another embodiment provides a crystal form of tenofovir alafenamide hydrochloride having an XRPD substantially as shown in FIG. 13.

Another embodiment provides a crystal form of tenofovir alafenamide hydrochloride having differential scanning calorimetry (DSC) onset endotherms of 144±2° C. and 157±2° C.

Another embodiment provides a crystal form of tenofovir alafenamide hydrochloride having differential scanning calorimetry (DSC) onset endotherms of 144±1° C. and 157±1° C.

Another embodiment provides a crystal form of tenofovir alafenamide hydrochloride having differential scanning calorimetry (DSC) onset endotherms of about 144° C. and about 157° C.

Another embodiment provides tenofovir alafenamide ethanesulfonate.

In some embodiments, the ratio of ethanesulfonic acid to tenofovir alafenamide is 1±0.5.

In some embodiments, the ratio of ethanesulfonic acid to tenofovir alafenamide is 1±0.4.

In some embodiments, the ratio of ethanesulfonic acid to tenofovir alafenamide is 1±0.3.

In some embodiments, the ratio of ethanesulfonic acid to tenofovir alafenamide is 1±0.2.

In some embodiments, the ratio of ethanesulfonic acid to tenofovir alafenamide is 1±0.1.

In some embodiments, the ratio of ethanesulfonic acid to tenofovir alafenamide is 1±0.05.

Another embodiment provides a crystal form of tenofovir alafenamide ethanesulfonate wherein the XRPD pattern comprises 2theta values of 9.0±0.2, 9.9±0.2, 17.0±0.2, and 21.4±0.2.

Another embodiment provides a crystal form of tenofovir alafenamide ethanesulfonate wherein the XRPD pattern comprises 2theta values selected from the group consisting of at least 4, 5, 6, or 7 of the following: 9.0, 9.9, 10.7, 17.0, 18.8, 19.6, and 21.4.

Figure 14:
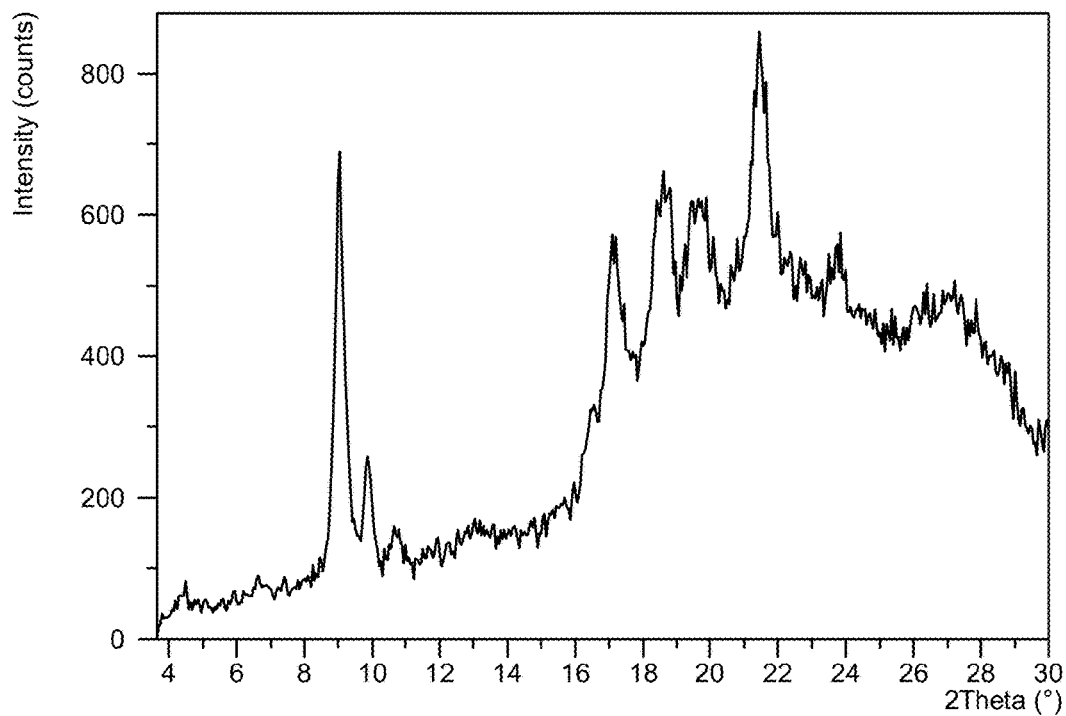

Another embodiment provides a crystal form of tenofovir alafenamide ethanesulfonate having an XRPD substantially as shown in FIG. 14.

Another embodiment provides a crystal form of tenofovir alafenamide ethanesulfonate having a differential scanning calorimetry (DSC) onset endotherm of 177±2° C.

Another embodiment provides a crystal form of tenofovir alafenamide ethanesulfonate having a differential scanning calorimetry (DSC) onset endotherm of 177±1° C.

Another embodiment provides a crystal form of tenofovir alafenamide ethanesulfonate having a differential scanning calorimetry (DSC) onset endotherm of about 177° C.

Another embodiment provides tenofovir alafenamide benzenesulfonate.

In some embodiments, the ratio of benzenesulfonic acid to tenofovir alafenamide is 1±0.5.

In some embodiments, the ratio of benzenesulfonic acid to tenofovir alafenamide is 1±0.4.

In some embodiments, the ratio of benzenesulfonic acid to tenofovir alafenamide is 1±0.3.

In some embodiments, the ratio of benzenesulfonic acid to tenofovir alafenamide is 1±0.2.

In some embodiments, the ratio of benzenesulfonic acid to tenofovir alafenamide is 1±0.1.

In some embodiments, the ratio of benzenesulfonic acid to tenofovir alafenamide is 1±0.05.

Another embodiment provides a crystal form of tenofovir alafenamide benzenesulfonate, wherein the XRPD pattern comprises 2theta values of 4.1±0.2, 8.3±0.2, 13.3±0.2 and 17.8±0.2.

Another embodiment provides a crystal form of tenofovir alafenamide benzenesulfonate, wherein the XRPD pattern comprises 2theta values selected from the group consisting of at least 4, 5, 6, 7, 8, 9, 10, 11, 12, 13, 14, 15, 16, or 17 of the following: 4.1, 6.5, 8.3, 11.9, 13.3, 14.7, 15.4, 16.5, 17.8, 18.9, 19.4, 20.3, 21.1, 23.1, 24.1, 24.9, and 29.2.

Figure 15:
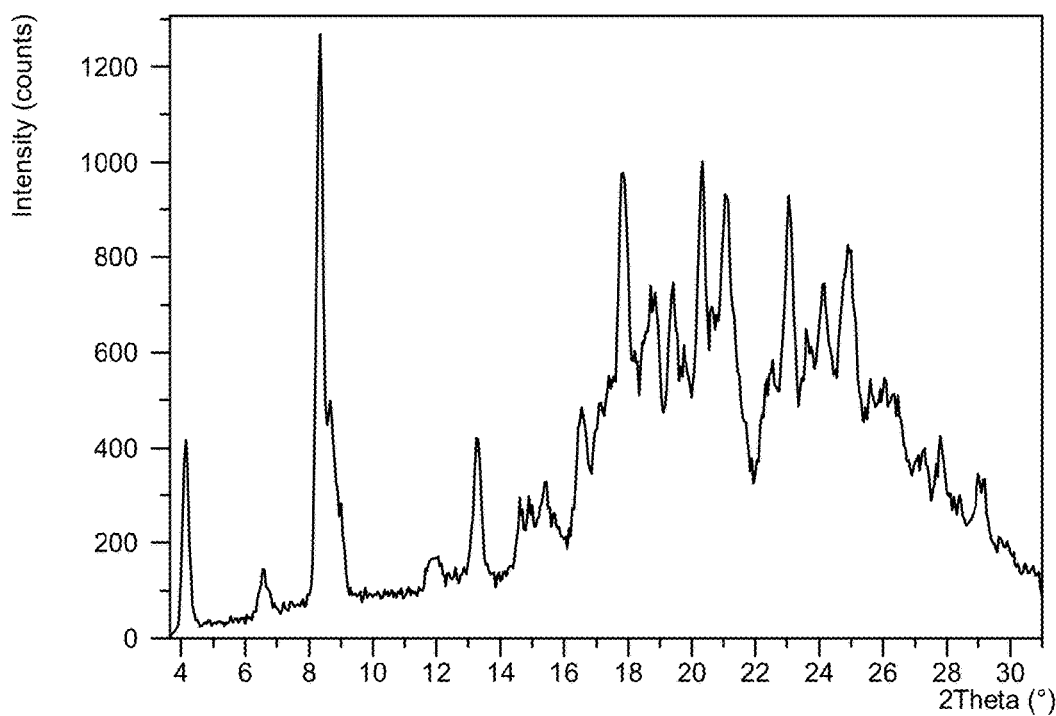

Another embodiment provides a crystal form of tenofovir alafenamide benzenesulfonate having an XRPD substantially as shown in FIG. 15.

Another embodiment provides a crystal form of tenofovir alafenamide benzenesulfonate having differential scanning calorimetry (DSC) onset endotherms of 42±2° C. and 134±2° C.

Another embodiment provides a crystal form of tenofovir alafenamide benzenesulfonate having differential scanning calorimetry (DSC) onset endotherms of 42±1° C. and 134±1° C.

Another embodiment provides a crystal form of tenofovir alafenamide benzenesulfonate having differential scanning calorimetry (DSC) onset endotherms of about 42° C. and about 134° C.

Another embodiment provides a crystal form of tenofovir alafenamide methanesulfonate, wherein the XRPD pattern comprises 2theta values of 8.7±0.2, 9.9±0.2, 10.1±0.2, and 19.7±0.2.

Another embodiment provides a crystal form of tenofovir alafenamide methanesulfonate, wherein the XRPD pattern comprises 2theta values selected from the group consisting of at least 4, 5, 6, 7, 8, 9, or 10 of the following: 4.1, 8.7, 9.9, 10.1, 13.2, 17.2, 18.8, 19.7, 20.4 and 21.7.

Figure 16A:
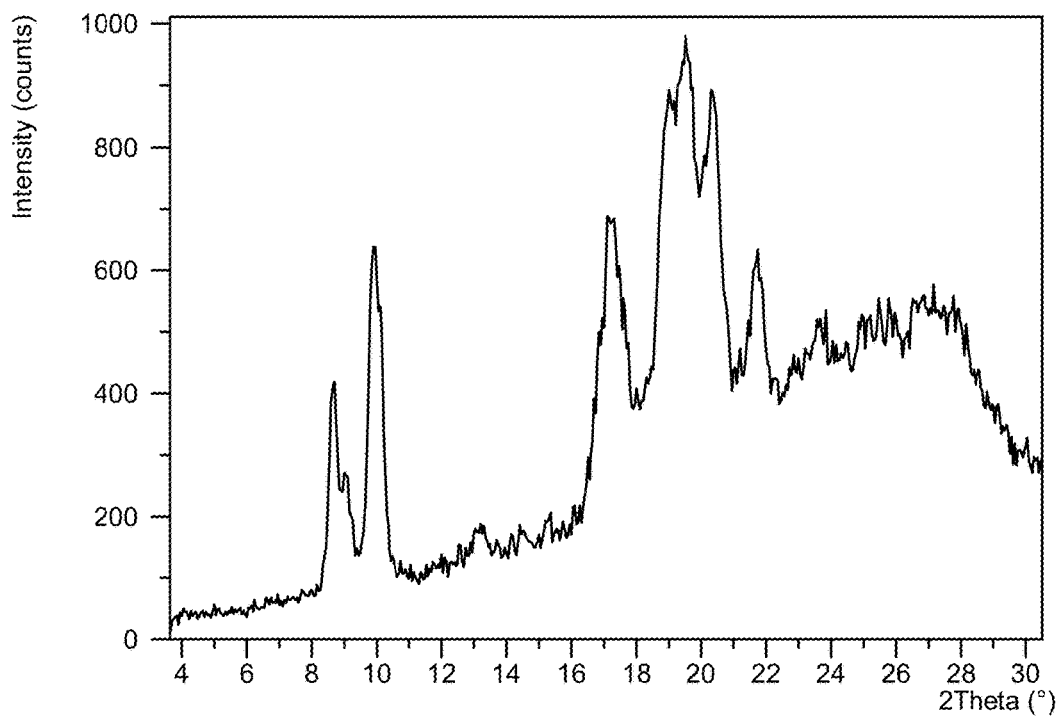
FIG. 16b. Presented in FIG. 16b is the Experimental X-ray powder diffraction (XRPD) pattern of TAF methanesulfonate pattern 2

Another embodiment provides a crystal form of tenofovir alafenamide methanesulfonate having an XRPD substantially as shown in FIG. 16a.

Another embodiment provides a crystal form of tenofovir alafenamide methanesulfonate, wherein the XRPD pattern comprises 2theta values of 9.0, 9.5, 18.6, and 22.4±0.2.

Another embodiment provides a crystal form of tenofovir alafenamide methanesulfonate, wherein the XRPD pattern comprises 2theta values selected from the group consisting of at least 4, 5, 6, 7, 8, 9, 10, 11, 12, 13, 14, 15, 16 or 17 of the following: 4.5, 6.8, 9.0, 9.5, 12.4, 12.9, 13.3, 15.9, 17.9, 18.6, 19.0, 19.8, 20.9, 22.4, 23.4, 24.2 and 27.0.

Figure 16B:
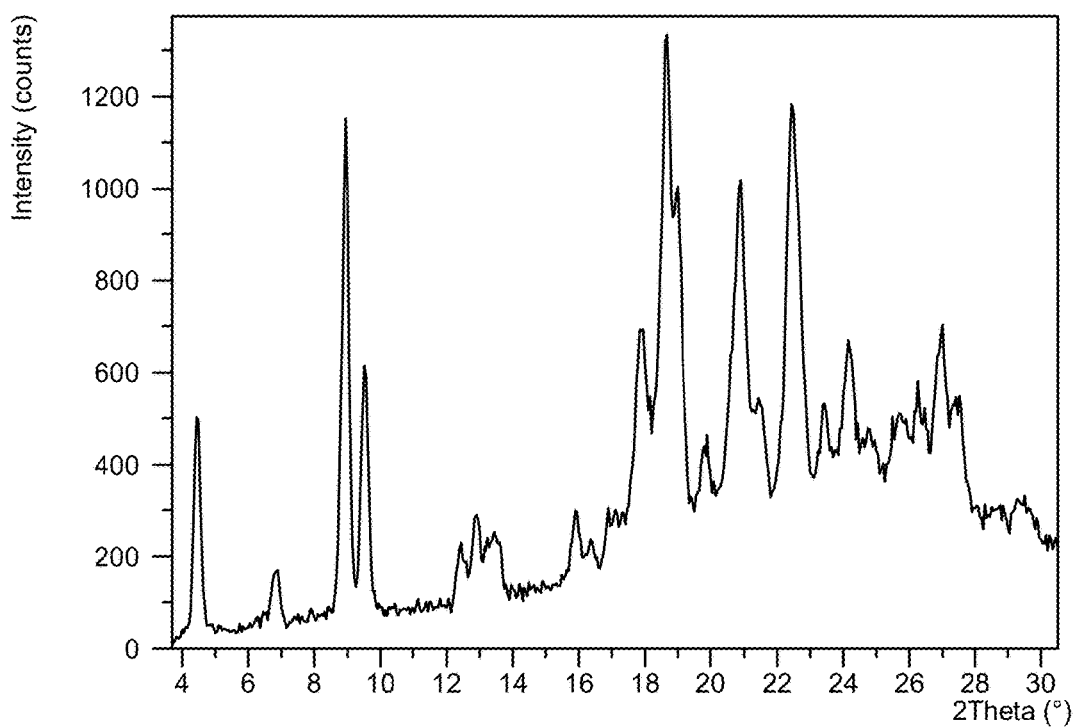

Another embodiment provides a crystal form of tenofovir alafenamide methanesulfonate having an XRPD substantially as shown in FIG. 16b.

Another embodiment provides tenofovir alafenamide sulfate.

In some embodiments, the ratio of sulfuric acid to tenofovir alafenamide is 1±0.5.

In some embodiments, the ratio of sulfuric acid to tenofovir alafenamide is 1±0.4.

In some embodiments, the ratio of sulfuric acid to tenofovir alafenamide is 1±0.3.

In some embodiments, the ratio of sulfuric acid to tenofovir alafenamide is 1±0.2.

In some embodiments, the ratio of sulfuric acid to tenofovir alafenamide is 1±0.1.

In some embodiments, the ratio of sulfuric acid to tenofovir alafenamide is 1±0.05.

Another embodiment provides a crystal form of tenofovir alafenamide sulfate wherein the XRPD pattern comprises 2theta values of 9.1±0.2, 11.0±0.2, 18.2±0.2 and 19.7±0.2.

Another embodiment provides a crystal form of tenofovir alafenamide sulfate wherein the XRPD pattern comprises 2theta values selected from the group consisting of at least 4, 5, 6, 7, 8, 9, 10, 11, 12, 13, 14, 15, 16, 17, 18, 19, or 20 of the following: 9.1, 10.6, 11.0, 14.2, 16.5, 16.8, 17.7, 18.2, 19.0, 19.7, 21.5, 22.1, 22.9, 24.1, 25.5, 26.5, 27.2, 27.8, 29.1 and 29.8.

Figure 17:
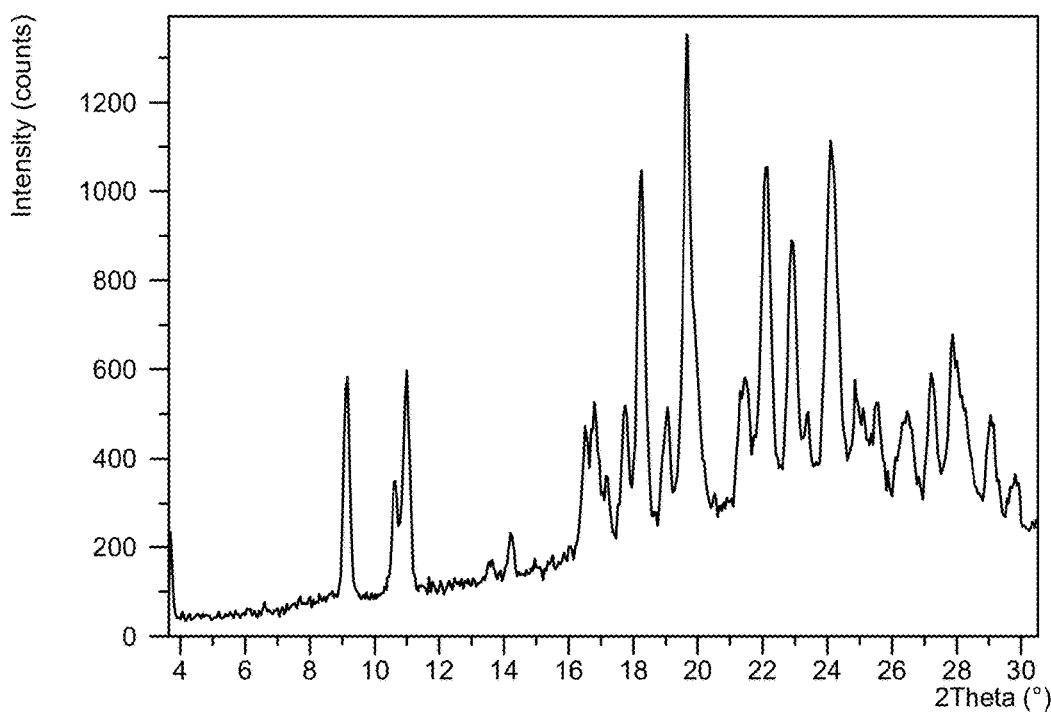
FIG. 17. Presented in FIG. 17 is the experimental X-ray powder diffraction (XRPD) pattern of TAF sulfate FIG. 18. Presented in FIG. 18 is the experimental differential scanning calorimetry (DSC) and Thermo-gravimetric Analysis (TGA) thermograms of tenofovir alafenamide hydrochloride FIG. 19. Presented in FIG. 19 is the experimental differential scanning calorimetry (DSC) thermogram of tenofovir alafenamide oxalate FIG. 20. Presented in FIG. 20 is the experimental Thermo-gravimetric Analysis (TGA) thermogram of tenofovir alafenamide oxalate FIG. 21. Presented in FIG. 21 is the experimental differential scanning calorimetry (DSC) of TAF sesquifumarate isopropanol solvate FIG. 22. Presented in FIG. 22 is the experimental differential scanning calorimetry (DSC) of TAF sesquifumarate FIG. 23. Presented in FIG. 23 is the experimental differential scanning calorimetry (DSC) and Thermo-gravimetric Analysis (TGA) of TAF saccharin FIG. 24. Presented in FIG. 24 is the experimental differential scanning calorimetry (DSC) and Thermo-gravimetric Analysis (TGA) of TAF malonate FIG. 25. Presented in FIG. 25 is the experimental differential scanning calorimetry (DSC) and Thermo-gravimetric Analysis (TGA) of TAF L-malate FIG. 26. Presented in FIG. 26 is the experimental differential scanning calorimetry (DSC) and Thermo-gravimetric Analysis (TGA) of TAF sulfate FIG. 27. Presented in FIG. 27 is the experimental differential scanning calorimetry (DSC) and Thermo-gravimetric Analysis (TGA) of TAF maleate FIG. 28. Presented in FIG. 28 is the experimental differential scanning calorimetry (DSC) and Thermo-gravimetric Analysis (TGA) of TAF ethanesulfonate FIG. 29. Presented in FIG. 29 is the experimental differential scanning calorimetry (DSC) and Thermo-gravimetric Analysis (TGA) of TAF benzenesulfonate FIG. 30. Presented in FIG. 30 is the experimental differential scanning calorimetry (DSC) and Thermo-gravimetric Analysis (TGA) of TAF methanesulfonate pattern 1

Another embodiment provides a crystal form of tenofovir alafenamide sulfate having an XRPD substantially as shown in FIG. 17.

Another embodiment provides a crystal form of tenofovir alafenamide sulfate, having a differential scanning calorimetry (DSC) onset endotherm of 159±2° C.

Another embodiment provides a crystal form of tenofovir alafenamide sulfate, having a differential scanning calorimetry (DSC) onset endotherm of 159±1° C.

Another embodiment provides a crystal form of tenofovir alafenamide sulfate, having a differential scanning calorimetry (DSC) onset endotherm of about 159° C.

In some embodiments, is provided a pharmaceutical composition comprising the co-crystals, salts and/or crystal forms of tenofovir alafenamide disclosed herein and a pharmaceutically acceptable excipient.

In some embodiments, the pharmaceutical composition comprises at least one additional therapeutic agent selected from the group consisting of human immunodeficiency virus (HIV) protease inhibiting compounds, HIV non nucleoside inhibitors of reverse transcriptase, HIV nucleoside inhibitors of reverse transcriptase, HIV nucleotide inhibitors of reverse transcriptase, HIV integrase inhibitors and CCR5 inhibitors.

In some embodiments, the pharmaceutical composition comprises at least one additional therapeutic agent selected from the group consisting of HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, HbcAg modulators, cyclophilin inhibitors, HBV viral entry inhibitors, NTCP inhibitors, hepatitis B virus E antigen inhibitors, HBx inhibitors, cccDNA inhibitors, HBV capsid inhibitors, stimulators of retinoic acid-inducible gene 1, and stimulators of NOD2.

Another embodiment provides a method for treating or preventing a viral infection in a human, comprising administering to the human a co-crystal, salt and/or crystal form of tenofovir alafenamide as described herein. More particularly, the viral infection is human immunodeficiency virus (HIV). Alternatively, the viral infection is hepatitis B virus (HBV).

In some embodiments, is provided a method for treating an HIV infection comprising administering to a subject in need thereof a therapeutically effective amount of the co-crystals, salts and/or crystal forms of tenofovir alafenamide disclosed herein.

In some embodiments, the method further comprises administering to the subject one or more additional therapeutic HIV agents. In some embodiments, the method further comprises administering to the subject one or more additional therapeutic agents selected from the group consisting of HIV protease inhibiting compounds, HIV non nucleoside inhibitors of reverse transcriptase, HIV nucleoside inhibitors of reverse transcriptase, HIV nucleotide inhibitors of reverse transcriptase, HIV integrase inhibitors and CCR5 inhibitors.

Another embodiment provides a method for treating or preventing a viral infection in a human, comprising administering to the human a co-crystal, salt and/or crystal form of tenofovir alafenamide as described herein. More particularly, the viral infection is human immunodeficiency virus (HIV). Alternatively, the viral infection is hepatitis B virus (HBV).

In some embodiments, is provided a method for treating a hepatitis B virus (HBV) infection comprising administering to a subject in need thereof a therapeutically effective amount of the co-crystals, salts and/or crystal forms of tenofovir alafenamide disclosed herein.

In some embodiments, the method further comprises administering to the subject one or more additional HBV therapeutic agents. In some embodiments, the method further comprises administering to the subject one or more additional therapeutic agents selected from the group consisting of HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, HbcAg modulators, cyclophilin inhibitors, HBV therapeutic vaccines, HBV viral entry inhibitors, NTCP inhibitors, short interfering RNAs, hepatitis B virus E antigen inhibitors, HBx inhibitors, cccDNA inhibitors, HBV antibodies, HBV capsid inhibitors, stimulators of retinoic acid-inducible gene 1, and stimulators of NOD2.

Another embodiment provides a co-crystal, salt and/or crystal form of tenofovir alafenamide as described herein or a composition thereof for use in therapy. For instance, one embodiment provides a co-crystal, salt and/or crystal form of tenofovir alafenamide as described herein or a composition thereof for use in a method of treating or preventing a viral infection.

In some embodiments, are provided co-crystals, salts and/or crystal forms of tenofovir alafenamide disclosed herein or a composition thereof, for use in the prophylactic or therapeutic treatment of HIV.

In some embodiments, are provided co-crystals, salts and/or crystal forms of tenofovir alafenamide disclosed herein or a composition thereof, for use in the prophylactic or therapeutic treatment of HBV.

Tenofovir alafenamide co-crystals, salts and crystal forms can be administered by any route appropriate to the condition to be treated. Suitable routes include oral, rectal, nasal, topical (including ocular, buccal, and sublingual), vaginal, and parenteral (including subcutaneous, intramuscular, intravenous, intradermal, intrathecal, and epidural). Generally, tenofovir alafenamide co-crystals, salts and crystal forms are administered orally, but it can be administered by any of the other routes noted herein.

Accordingly, pharmaceutical compositions include those suitable for topical or systemic administration, including oral, rectal, nasal, buccal, sublingual, vaginal, or parenteral (including subcutaneous, intramuscular, intravenous, intradermal, intrathecal, and epidural) administration. The formulations are in unit dosage form and are prepared by any of the methods well known in the art of pharmacy.

For oral therapeutic administration, the tenofovir alafenamide co-crystals, salts and/or crystal forms may be combined with one or more excipients and used in the form of ingestible tablets, buccal tablets, troches, capsules, elixirs, suspensions, syrups, wafers, and the like. Such pharmaceutical compositions and preparations will typically contain at least 0.1% of tenofovir alafenamide co-crystal, salt or crystal form. The percentage of this active compound in the compositions and preparations may, of course, be varied and may conveniently be between about 2% to about 60% or more of the weight of a given unit dosage form. The amount of active compound in such therapeutically useful pharmaceutical compositions is preferably such that an effective dosage level will be obtained upon administration of a single-unit dosage (e.g., tablet). Other dosage formulations may provide therapeutically effective amounts of tenofovir alafenamide co-crystal, salt or crystal form upon repeated administration of subclinically effective amounts of the same. Preferred unit dosage formulations include those containing a daily dose (e.g., a single daily dose), as well as those containing a unit daily subclinical dose, or an appropriate fraction thereof (e.g., multiple daily doses), of tenofovir alafenamide co-crystals, salts and/or crystal forms.

Pharmaceutical compositions suitable for oral administration may be presented as discrete units such as capsules, cachets, or tablets, each containing a predetermined amount of tenofovir alafenamide co-crystals, salts and/or crystal forms; as a powder or granules; as a solution or a suspension in an aqueous liquid or a nonaqueous liquid; or as an oil-in-water liquid emulsion or a water-in-oil liquid emulsion. Tenofovir alafenamide co-crystals, salts and/or crystal forms may also be presented as a bolus, electuary, or paste.

Tenofovir alafenamide co-crystals, salts and/or crystal forms are preferably administered as part of a pharmaceutical composition or formulation. Such pharmaceutical composition or formulation comprises tenofovir alafenamide co-crystals, salts and/or crystal forms together with one or more pharmaceutically acceptable carriers/excipients, and optionally other therapeutic ingredients. The excipient(s)/carrier(s) must be "acceptable" in the sense of being compatible with the other ingredients of the formulation and not deleterious to the patient. Excipients include, but are not limited to, substances that can serve as a vehicle or medium for tenofovir alafenamide co-crystals, salts and/or crystal forms (e.g., a diluent carrier). They may be enclosed in hard or soft shell gelatin capsules, may be compressed into tablets, or may be incorporated directly with the food of the patient's diet.

Accordingly, the tablets, troches, pills, capsules, and the like may also contain, without limitation, the following: a binder(s), such as hydroxypropyl cellulose, povidone, or hydroxypropyl methylcellulose; a filler(s), such as microcrystalline cellulose, pregelatinized starch, starch, mannitol, or lactose monohydrate; a disintegrating agent(s), such as croscarmellose sodium, cross-linked povidone, or sodium starch glycolate; a lubricant(s), such as magnesium stearate, stearic acid, or other metallic stearates; a sweetening agent(s), such as sucrose, fructose, lactose, or aspartame; and/or a flavoring agent(s), such as peppermint, oil of wintergreen, or a cherry flavoring. When the unit dosage form is a capsule, it may contain, in addition to materials of the above types, a liquid carrier, such as a vegetable oil or a polyethylene glycol. Various other materials may be present as coatings or to otherwise modify the physical form of the solid unit dosage form. For instance, tablets, pills, or capsules may be coated with gelatin, polymers, wax, shellac, or sugar and the like. Of course, any material used in preparing any unit dosage form typically will be pharmaceutically acceptable and substantially nontoxic in the amounts employed. In addition, tenofovir alafenamide co-crystals, salts and/or crystal forms may be incorporated into sustained-release preparations and devices.

For infections of the eye or other external tissues, e.g., mouth and skin, the pharmaceutical compositions are preferably applied as a topical ointment or cream containing tenofovir alafenamide co-crystals, salts and/or crystal forms in an amount of, for example, 0.01 to 10% w/w (including active ingredient in a range between 0.1% and 5% in increments of 0.1% w/w such as 0.6% w/w, 0.7% w/w, etc.), preferably 0.2 to 3% w/w and most preferably 0.5 to 2% w/w. When formulated in an ointment, the active ingredient may be employed with either a paraffinic or a water-miscible ointment base. Alternatively, the active ingredient may be formulated in a cream with an oil-in-water cream base.

Pharmaceutical compositions suitable for topical administration in the mouth include lozenges comprising tenofovir alafenamide co-crystals, salts and/or crystal forms in a flavored basis, for example, sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Pharmaceutical formulations suitable for parenteral administration are sterile and include aqueous and nonaqueous injection solutions that may contain antioxidants, buffers, bacteriostats, and solutes that render the formulation isotonic with the blood of the intended recipient; and aqueous and nonaqueous sterile suspensions that may include suspending agents and thickening agents. The formulations may be presented in unit-dose or multi-dose containers, for example, sealed ampoules and vials with elastomeric stoppers, and may be stored in a freeze-dried (lyophilized) condition requiring only the addition of the sterile liquid carrier (e.g., water for injections) immediately prior to use. Injection solutions and suspensions may be prepared from sterile powders, granules, and tablets of the kind previously described.

In addition to the ingredients particularly mentioned above, the pharmaceutical compositions/formulations may include other ingredients conventional in the art, having regard to the type of formulation in question.

In another embodiment, there is provided veterinary compositions comprising tenofovir alafenamide co-crystals, salts and/or crystal forms together with a veterinary carrier therefor. Veterinary carriers are materials useful for the purpose of administering the composition to cats, dogs, horses, rabbits, and other animals, and may be solid, liquid, or gaseous materials that are otherwise inert or acceptable in the veterinary art and are compatible with the active ingredient. These veterinary compositions may be administered orally, parenterally, or by any other desired route.

The tenofovir alafenamide co-crystals, salts and/or crystal forms can be used to provide controlled release pharmaceutical formulations containing a matrix or absorbent material and an active ingredient of the invention, in which the release of the active ingredient can be controlled and regulated to allow less frequent dosing or to improve the pharmacokinetic or toxicity profile of the compound. Controlled release formulations adapted for oral administration, in which discrete units comprising a compounds of the invention, can be prepared according to conventional methods.

Useful dosages of tenofovir alafenamide co-crystals, salts and/or crystal forms can be determined by comparing in vitro activities, and the in vivo activities in animal models. Methods for the extrapolation of effective amounts/dosages in mice and other animals to therapeutically effective amounts/dosages in humans are known in the art.

The amount of tenofovir alafenamide co-crystals, salts and/or crystal forms required for use in treatment will vary with several factors, including but not limited to the route of administration, the nature of the condition being treated, and the age and condition of the patient; ultimately, the amount administered will be at the discretion of the attendant physician or clinician. The therapeutically effective amount/dose of tenofovir alafenamide co-crystals, salts and crystal forms depends, at least, on the nature of the condition being treated, any toxicity or drug interaction issues, whether the compound is being used prophylactically (e.g., sometimes requiring lower doses) or against an active disease or condition, the method of delivery, and the pharmaceutical formulation, and will be determined by the clinician using conventional dose escalation studies.

In one embodiment, the oral dose of tenofovir alafenamide co-crystals, salts and/or crystal forms may be in the range from about 0.0001 to about 100 mg/kg body weight per day, for example, from about 0.01 to about 10 mg/kg body weight per day, from about 0.01 to about 5 mg/kg body weight per day, from about 0.5 to about 50 mg/kg body weight per day, from about 1 to about 30 mg/kg body weight per day, from about 1.5 to about 10 mg/kg body weight per day, or from about 0.05 to about 0.5 mg/kg body weight per day. As a non limiting example, the daily candidate dose for an adult human of about 70 kg body weight will range from about 0.1 mg to about 1000 mg, or from about 1 mg to about 1000 mg, or from about 5 mg to about 500 mg, or from about 1 mg to about 150 mg, or from about 5 mg to about 150 mg, or from about 5 mg to about 100 mg, and may take the form of single or multiple doses.

Therapeutic methods include administering tenofovir alafenamide co-crystals, salts and/or crystal forms to a subject/patient in need of the same as a therapeutic or preventative treatment. Thus, tenofovir alafenamide co-crystals, salts and/or crystal forms may be administered to a subject/patient having a medical disorder or to a subject who may acquire the disorder. One of ordinary skill will appreciate that such treatment is given in order to ameliorate, prevent, delay, cure, and/or reduce the severity of a symptom or set of symptoms of a disorder (including a recurring disorder). The treatment may also be given to prolong the survival of a subject, e.g., beyond the survival time expected in the absence of such treatment. The medical disorders that may be treated with tenofovir alafenamide co-crystals, salts and crystal forms include those discussed herein, including without limitation, HIV infection and HBV infection.

In the following description of the examples, specific embodiments in which the invention may be practiced are described. These embodiments are described in sufficient detail to enable those skilled in the art to practice the invention. Other embodiments may be utilized, and logical and other changes may be made without departing from the scope of the invention. The following detailed description is, therefore, not to be taken in a limiting sense, and the scope of the invention is defined only by the appended claims, along with the full scope of equivalents to which such claims are entitled.

EXAMPLES

X-Ray Powder Diffraction (XRPD)

Two XRPD systems were used for the characterization of the samples.

(1) Bruker AXS C2 GADDS diffractometer uses Cu Kalpha radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm. The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample was exposed to the X-ray beam for 120 seconds. The software used for data collection was GADDS for XP/2000 4.1.36 and the data was analyzed and presented using Diffrac Plus EVA v13.0.0.2 or v15.0.0.0.

Samples run under ambient conditions were prepared as flat plate specimens using powder as received without grinding. Approximately 1-2 mg of the sample was lightly pressed on a glass slide to obtain a flat surface.

(2) Bruker D8 diffractometer uses Cu Kα radiation (40 kV, 40 mA), θ–2θ goniometer, and divergence of V4 and receiving slits, a Ge monochromator and a Lynxeye detector. The software used for data collection was Diffrac Plus XRD Commander v2.6.1 and the data was analyzed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection was: Angular range: 2 to 42° 2θ; Step size: 0.05° 2θ; Collection time: 0.5 s/step (3) PANanalytical XPERT-PRO diffractometer at ambient conditions under the following experimental settings: 45 KV, 40 mA, Kα1=1.5406 Å, scan range 2 to 40°, step size 0.0084 or 0.0167°, measurement time: 5 min.

Differential Scanning Calorimetry (DSC)

DSC data was collected on two systems.

(1) Mettler DSC 823E equipped with a 34 position auto-sampler. The instrument was calibrated for energy and temperature using certified Indium. Typically 0.5-3 mg of each sample, in a pin-holed aluminum pan, was heated at 10° C./min from 25° C. to 300° C. A nitrogen purge at 50 ml/min was maintained over the sample.

(2) TA Instruments Q2000 system equipped with a 50-position auto-sampler. The calibration for energy and temperature was carried out using certified indium. Typically 1-5 mg of each sample, in a pin-holed aluminum pan, was heated at 10° C./min from 25° C. to 250° C. A nitrogen purge at 50 ml/min was maintained over the sample throughout the measurement. The onset of the melting endotherm was reported as the melting point.

Thermo-Gravimetric Analysis (TGA)

TGA Data was Collected on Two Systems (1) Mettler TGA/SDTA 851e equipped with a 34 position auto-sampler. The instrument was calibrated using certified indium. Typically 5-30 mg of each sample was loaded onto a pre-weighed aluminum crucible and was heated at 10° C./min from ambient temperature to 350° C. A nitrogen purge at 50 ml/min was maintained over the sample.

(2) TA Instruments Q5000 system, equipped with a 25 position auto-sampler. Typically 1-5 mg of each sample was loaded onto a pre-tared aluminum pan and heated at 10° C./min from ambient temperature to 250° C. A nitrogen purge at 25 ml/min was maintained over the sample throughout the measurement.

Example 1

Preparation and Characterization of Tenofovir Alafenamide Hydrochloride

Tenofovir alafenamide free base was dissolved in 50 volumes of ethyl acetate (EtOAc) at about 50° C. and 1.1 eq.

of 1M HCl in THF was added. The solution was cooled down to room temperature and filtered to give a crystalline solid.

Crystalline solid was obtained similarly in a variety of solvents, including ethanol, 1-propanol, 2-propanol, 1-butanol, 2-methoxy ethanol, acetone, MEK, MIBK, methyl acetate, isopropyl acetate, 2-methyl THF, THF, dimethoxyethane, acetonitrile, and butyl acetate. The XRPD is shown in FIG. 13.

The XRPD pattern remained unchanged after storage at 40° C. 75% RH for 14 days. Prominent peaks were selected from observed peaks by identifying substantially non-overlapping, low-angle peaks with strong intensity. The prominent peaks of tenofovir alafenamide hydrochloride include: 7.0±0.2°, 8.6±0.2°, 10.4±0.2°, and 18.2±0.2° 2 Theta. The observed peaks of tenofovir alafenamide hydrochloride are shown in Table 1.

TABLE 1

Observed peaks in the XRPD pattern of tenofovir alafenamide hydrochloride

| No. | Pos. [°2Th.] | Rel. Int. [%] |
|---|---|---|
| 1 | 7.0 | 18 |
| 2 | 8.6 | 37 |
| 3 | 9.1 | 23 |
| 4 | 10.4 | 100 |
| 5 | 12.1 | 9 |
| 6 | 13.4 | 49 |
| 7 | 13.9 | 25 |
| 8 | 14.8 | 40 |
| 9 | 16.3 | 23 |
| 10 | 18.2 | 84 |
| 11 | 18.9 | 62 |
| 12 | 20.9 | 41 |
| 13 | 22.0 | 50 |
| 14 | 24.2 | 48 |
| 15 | 25.2 | 15 |
| 16 | 26.6 | 57 |
| 17 | 27.7 | 41 |
| 18 | 29.2 | 29 |

Figure 18:
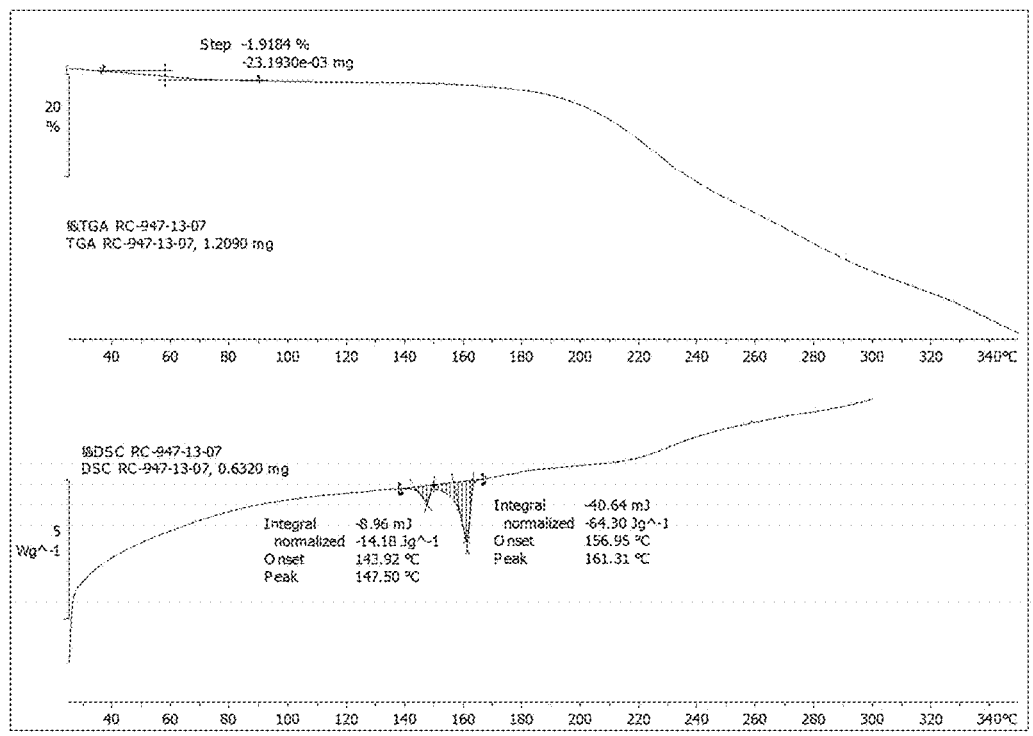

Experimental differential scanning calorimetry (DSC) and Thermo-gravimetric Analysis (TGA) thermograms of tenofovir alafenamide hydrochloride are shown in FIG. 18. DSC analysis shows two overlapping endotherms with onsets of 144° C. and 157° C. The TGA data shows 1.9% weight loss between RT and 90° C.

Example 2

Preparation and Characterization of Tenofovir Alafenamide Oxalate

Tenofovir alafenamide free base was dissolved in 10 volumes of isopropyl alcohol (IPA) at room temperature, 1.1 eq. of 1M oxalic acid in THF was added. Precipitation was observed upon acid addition and filtration afforded the crystalline form or tenofovir alafenamide oxalate.

Crystalline solid with the same XRPD pattern was obtained similarly in EtOAc and THF. From ion chromatography (IC) the approximate stoichiometry is about 1 eq. of oxalic acid. The XRPD pattern is shown in FIG. 6.

Material exposed to stress condition (40° C. 75% RH 14 days) showed no change in XRPD. Prominent peaks were selected from observed peaks by identifying substantially non-overlapping, low-angle peaks with strong intensity. The prominent peaks of tenofovir alafenamide oxalate include: 4.1, 9.7, 20.8, and 25.0±0.2° 2 Theta. The observed peaks of tenofovir alafenamide oxalate are shown in Table 2.

TABLE 2

Observed peaks in the XRPD pattern of tenofovir alafenamide oxalate

| No. | Pos. [°2Th.] | Rel. Int. [%] |
|---|---|---|
| 1 | 4.1 | 100 |
| 2 | 7.6 | 3 |
| 3 | 9.7 | 6 |
| 4 | 12.4 | 2 |
| 5 | 12.8 | 1 |
| 6 | 16.6 | 6 |
| 7 | 20.8 | 15 |
| 8 | 22.8 | 1 |
| 9 | 24.0 | 2 |
| 10 | 25.0 | 14 |
| 11 | 29.1 | 1 |

Figure 19:
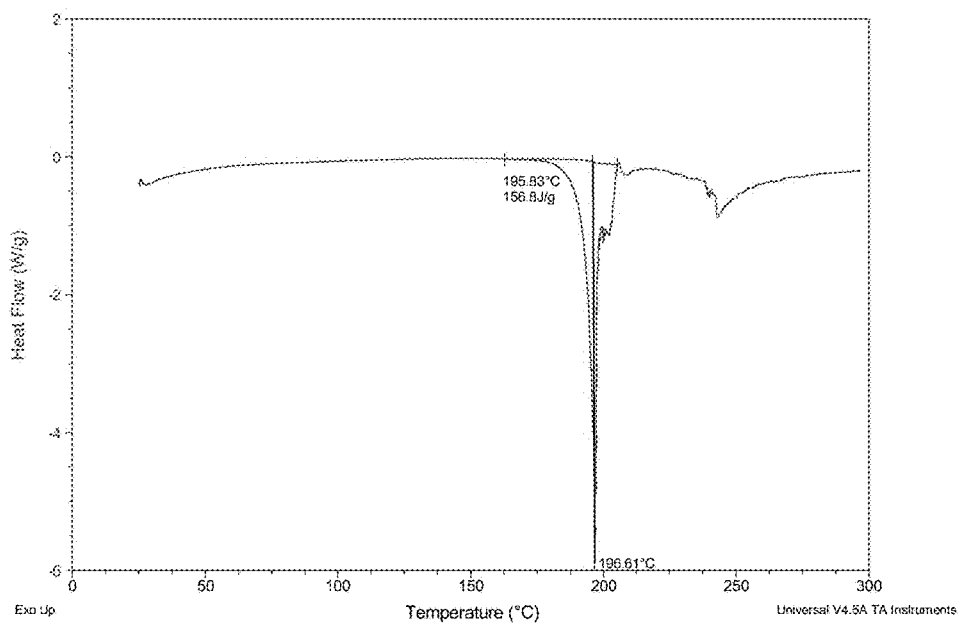

FIG. 19 shows the experimental differential scanning calorimetry (DSC) thermogram of tenofovir alafenamide oxalate.

DSC showed a sharp endotherm with high melting point, onset 196° C.

Figure 20:
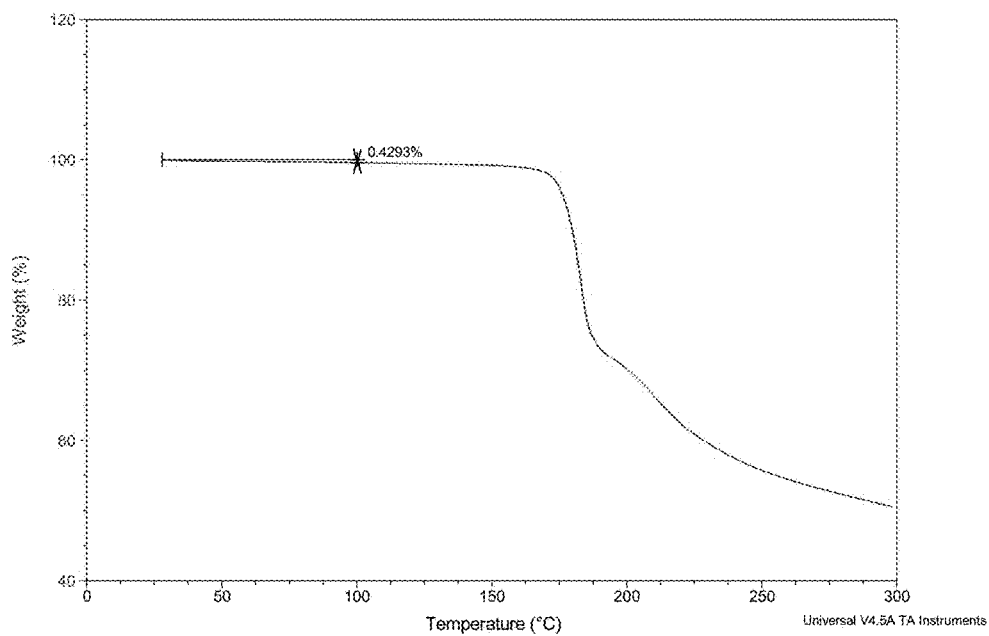

FIG. 20 shows the experimental Thermo-gravimetric Analysis (TGA) thermogram of tenofovir alafenamide oxalate.

TGA indicated no weight loss upon heating.

Example 3

Preparation and Characterization of Tenofovir Alafenamide Saccharin

Tenofovir alafenamide free base was suspended in 5 volumes of butyl acetate and 1 equivalent of saccharin was added as a solid. The slurry was treated by sonication. The solid obtained was isolated by filtration to give crystalline tenofovir alafenamide saccharin.

NMR spectrum indicated 1 equivalent of saccharin.
The XRPD is shown in FIG. 9.
The same XRPD pattern was obtained after storage at 40° C. 75% RH for 14 days.

Prominent peaks were selected from observed peaks by identifying substantially non-overlapping, low-angle peaks with strong intensity. The prominent peaks of tenofovir alafenamide saccharin include: 7.3, 14.4, 16.0, and 18.6±0.2° 2 Theta. The observed peaks of tenofovir alafenamide saccharin are shown in Table 3.

TABLE 3

Observed peaks in the XRPD pattern of tenofovir alafenamide saccharin

| No. | Pos. [°2Th.] | Rel. Int. [%] |
|---|---|---|
| 1 | 3.7 | 39 |
| 2 | 7.3 | 30 |
| 3 | 7.8 | 13 |
| 4 | 9.9 | 17 |
| 5 | 10.8 | 24 |
| 6 | 11.3 | 22 |
| 7 | 12.3 | 13 |
| 8 | 13.8 | 13 |
| 9 | 14.4 | 46 |
| 10 | 16.0 | 52 |
| 11 | 18.0 | 34 |

TABLE 3-continued

Observed peaks in the XRPD pattern of tenofovir alafenamide saccharin

| No. | Pos. [°2Th.] | Rel. Int. [%] |
|---|---|---|
| 12 | 18.6 | 100 |
| 13 | 21.7 | 19 |
| 14 | 22.5 | 29 |
| 15 | 23.7 | 58 |
| 16 | 25.0 | 28 |
| 17 | 26.3 | 45 |
| 18 | 27.7 | 16 |
| 19 | 29.2 | 25 |

Figure 23:
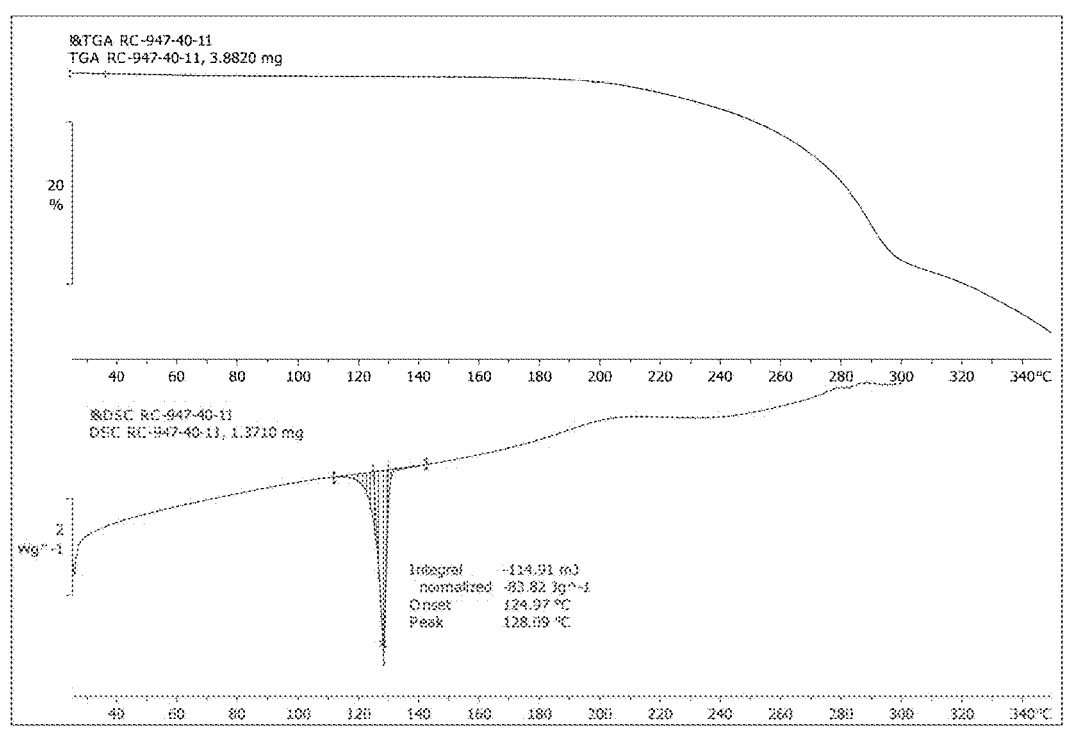

FIG. 23 shows the experimental differential scanning calorimetry (DSC) and Thermo-gravimetric Analysis (TGA) of TAF saccharin.

TGA indicated no weight loss upon heating. DSC showed a sharp endotherm with melting onset at about 125° C.

Example 4

Preparation and Characterization of Tenofovir Alafenamide Malonate

Tenofovir alafenamide free base was suspended in 50 volumes of ethyl acetate (EtOAc) at room temperature and 1.1 eq. of 1M malonic acid in THF was added. Precipitation was observed after cooling the clear solution to about 0° C. Filtration gave crystalline tenofovir alafenamide malonate.

NMR spectrum indicated 1 equivalent of malonic acid.

The XRPD is shown in FIG. 7.

A similar XRPD was obtained after storage at 40° C. 75% RH for 14 days.

Crystalline solid with a similar XRPD pattern was also obtained in IPA and THF. In IPA, MTBE was added as antisolvent. In THF the clear solution was subject to evaporation before precipitation was observed.

Prominent peaks were selected from observed peaks by identifying substantially non-overlapping, low-angle peaks with strong intensity. The prominent peaks of tenofovir alafenamide malonate include: 6.9, 8.7, 15.3, and 20.1±0.2° 2 Theta. The observed peaks of tenofovir alafenamide malonate are shown in Table 4.

TABLE 4

Observed peaks in the XRPD pattern of tenofovir alafenamide malonate

| No. | Pos. [°2Th.] | Rel. Int. [%] |
|---|---|---|
| 1 | 4.0 | 74 |
| 2 | 6.9 | 53 |
| 3 | 8.7 | 97 |
| 4 | 11.8 | 21 |
| 5 | 12.9 | 23 |
| 6 | 15.0 | 47 |
| 7 | 15.3 | 60 |
| 8 | 17.4 | 52 |
| 9 | 18.2 | 31 |
| 10 | 19.4 | 64 |
| 11 | 20.1 | 100 |
| 12 | 20.5 | 39 |
| 13 | 21.2 | 43 |
| 14 | 21.9 | 57 |
| 15 | 22.9 | 43 |
| 16 | 24.1 | 69 |

TABLE 4-continued

Observed peaks in the XRPD pattern of tenofovir alafenamide malonate

| No. | Pos. [°2Th.] | Rel. Int. [%] |
|---|---|---|
| 17 | 25.6 | 43 |
| 18 | 26.4 | 46 |
| 19 | 27.0 | 42 |
| 20 | 27.7 | 19 |
| 21 | 29.0 | 14 |
| 22 | 29.7 | 17 |

Figure 24:
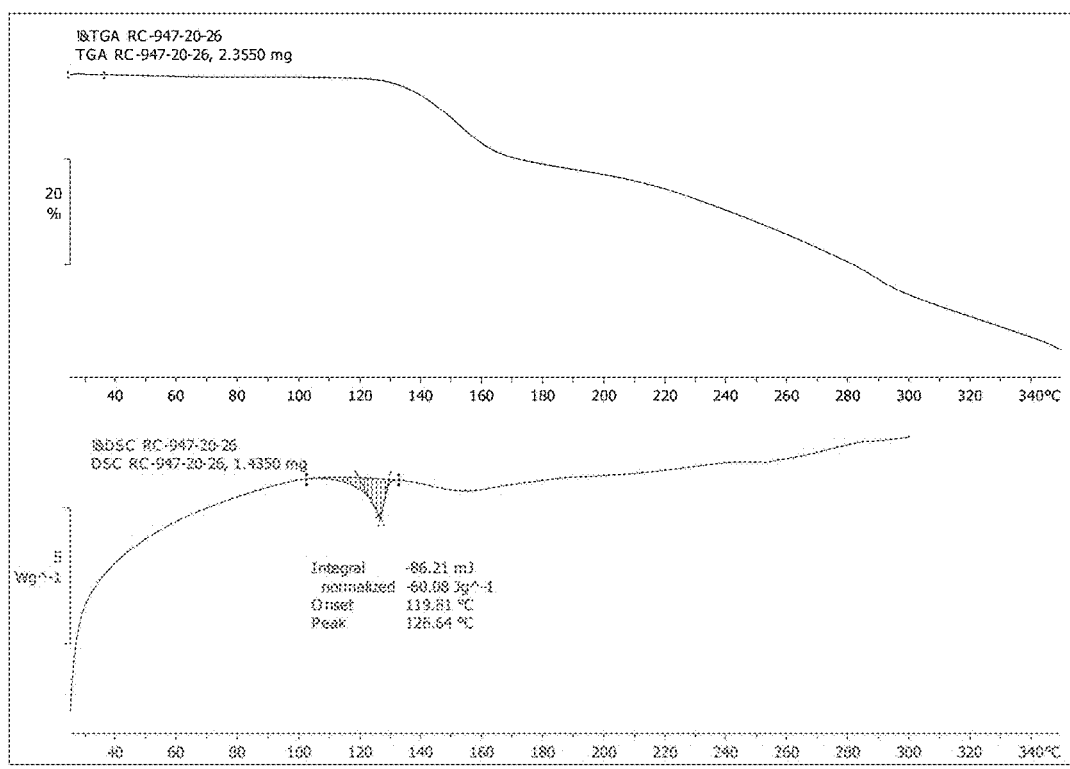

FIG. 24 shows the experimental differential scanning calorimetry (DSC) and Thermo-gravimetric Analysis (TGA) of TAF malonate.

TGA indicated no weight loss upon heating up to 120° C. DSC showed a relatively broad endotherm with onset at about 120° C.

Example 5

Preparation and Characterization of Tenofovir Alafenamide L-Malate

Tenofovir alafenamide free base was dissolved in 50 volumes of ethyl acetate (EtOAc) at room temperature, 1.1 eq. of 1M L-Malic acid in THF was added. Precipitation was observed after cooling the clear solution to about 0° C. Filtration gave crystalline tenofovir alafenamide L-malate.

NMR spectrum indicated 1 equivalent of L-malic acid.

The XRPD is shown in FIG. 8. Material exposed to stress condition (40° C. 75% RH for 14 days) showed no change.

The same XRPD pattern was observed when EtOAc was replaced by THF or IPA.

Prominent peaks were selected from observed peaks by identifying substantially non-overlapping, low-angle peaks with strong intensity. The prominent peaks of tenofovir alafenamide L-malate include: 10.0, 13.9, 16.5, and 21.2±0.2° 2 Theta. The observed peaks of tenofovir alafenamide L-malate are shown in Table 5.

TABLE 5

Observed peaks in the XRPD pattern of tenofovir alafenamide L-malate

| No. | Pos. [°2Th.] | Rel. Int. [%] |
|---|---|---|
| 1 | 5.3 | 4 |
| 2 | 10.0 | 37 |
| 3 | 12.0 | 10 |
| 4 | 13.4 | 22 |
| 5 | 13.9 | 36 |
| 6 | 15.3 | 38 |
| 7 | 16.5 | 38 |
| 8 | 17.9 | 5 |
| 9 | 19.4 | 4 |
| 10 | 20.2 | 13 |
| 11 | 21.2 | 100 |
| 12 | 22.0 | 25 |
| 13 | 23.1 | 10 |
| 14 | 24.0 | 7 |
| 15 | 26.2 | 33 |
| 16 | 27.0 | 10 |

Figure 25:
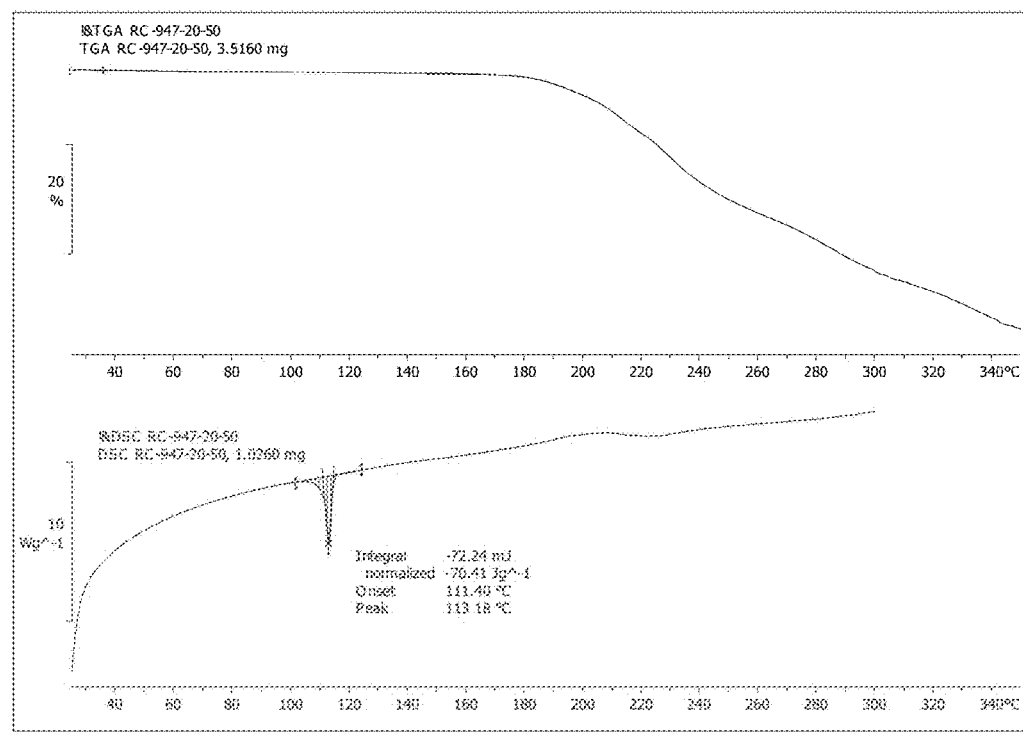

FIG. 25 shows the experimental differential scanning calorimetry (DSC) and Thermo-gravimetric Analysis (TGA) of TAF L-malate.

TGA indicated no weight loss upon heating. DSC showed a sharp endotherm with onset at about 111° C.

Example 6

Preparation and Characterization of Tenofovir Alafenamide Sulfate

Tenofovir alafenamide free base was dissolved in 10 volumes of isopropyl alcohol (IPA) at room temperature, 1.1 eq. of 1M sulfuric acid in THF was added. Precipitation was observed immediately. Filtration gave crystalline tenofovir alafenamide sulfate.

Ion chromatography indicated about 1 eq. of sulfate.
The XRPD is shown in FIG. 17.
The same XRPD pattern was observed when IPA was replaced by THF or EtOAc.

Prominent peaks were selected from observed peaks by identifying substantially non-overlapping, low-angle peaks with strong intensity. The prominent peaks of tenofovir alafenamide sulfate include: 9.1, 11.0, 18.2 and 19.7±0.2° 2 Theta. The observed peaks of tenofovir alafenamide sulfate are shown in Table 6.

TABLE 6

Observed peaks in the XRPD pattern of tenofovir alafenamide sulfate

| No. | Pos. [°2Th.] | Rel. Int. [%] |
|---|---|---|
| 1 | 9.1 | 46 |
| 2 | 10.6 | 24 |
| 3 | 11.0 | 45 |
| 4 | 14.2 | 9 |
| 5 | 16.5 | 24 |
| 6 | 16.8 | 28 |
| 7 | 17.7 | 25 |
| 8 | 18.2 | 74 |
| 9 | 19.0 | 22 |
| 10 | 19.7 | 100 |
| 11 | 21.5 | 22 |
| 12 | 22.1 | 66 |
| 13 | 22.9 | 49 |
| 14 | 24.1 | 69 |
| 15 | 25.5 | 17 |
| 16 | 26.5 | 13 |
| 17 | 27.2 | 23 |
| 18 | 27.8 | 32 |
| 19 | 29.1 | 18 |
| 20 | 29.8 | 8 |

Figure 26:
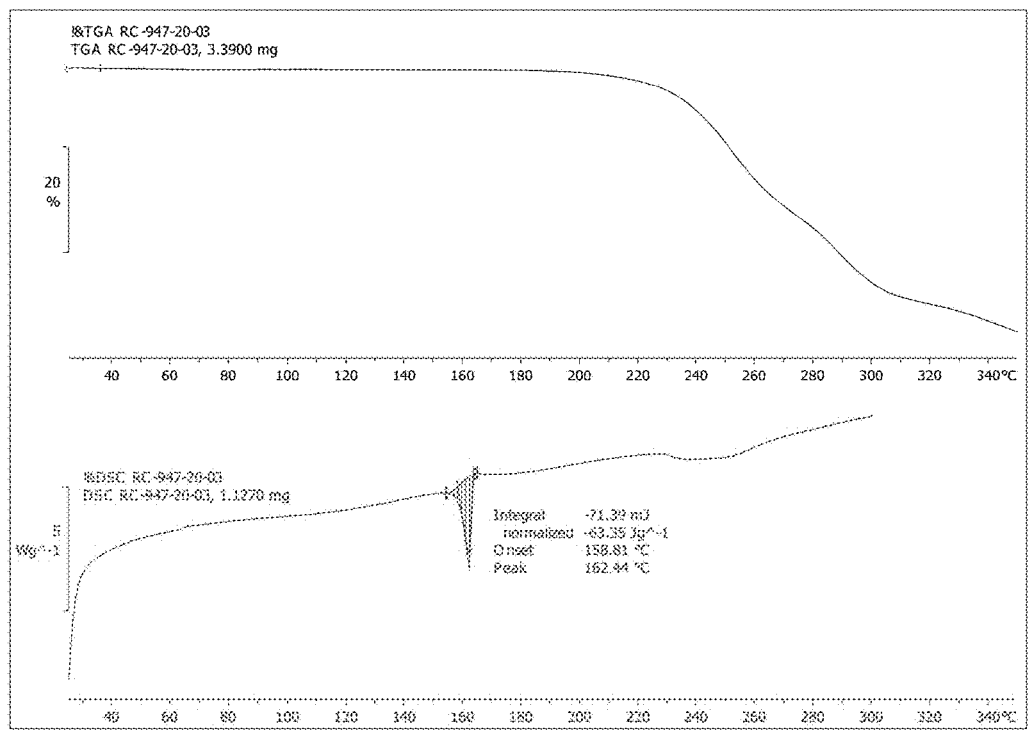

FIG. 26 shows the experimental differential scanning calorimetry (DSC) and Thermo-gravimetric Analysis (TGA) of TAF sulfate.

DSC showed a sharp endotherm with onset 158° C. TGA showed essentially no weight loss upon heating.

Example 7

Preparation and Characterization of Tenofovir Alafenamide Maleate

Tenofovir alafenamide free base was dissolved in 50 volumes of ethyl acetate (EtOAc) at room temperature, 1.1 eq. of 1M Maleic acid in THF was added. Precipitation was observed immediately. Filtration gave crystalline tenofovir alafenamide maleate.

NMR: spectrum indicated 1 eq. of Maleic acid.
The XRPD is shown in FIG. 12.

The same XRPD pattern was observed when EtOAc was replaced by THF or IPA.

Prominent peaks were selected from observed peaks by identifying substantially non-overlapping, low-angle peaks with strong intensity. The prominent peaks of tenofovir alafenamide maleate include: 7.6, 18.1, 21.1, and 26.0±0.2° 2 Theta. The observed peaks of tenofovir alafenamide maleate are shown in Table 7.

TABLE 7

Observed peaks in the XRPD pattern of tenofovir alafenamide maleate

| No. | Pos. [°2Th.] | Rel. Int. [%] |
|---|---|---|
| 1 | 4.2 | 100 |
| 2 | 6.4 | 13 |
| 3 | 7.6 | 91 |
| 4 | 10.5 | 21 |
| 5 | 12.6 | 22 |
| 6 | 15.2 | 13 |
| 7 | 18.1 | 61 |
| 8 | 21.1 | 37 |
| 9 | 24.4 | 17 |
| 10 | 26.0 | 55 |

Figure 27:
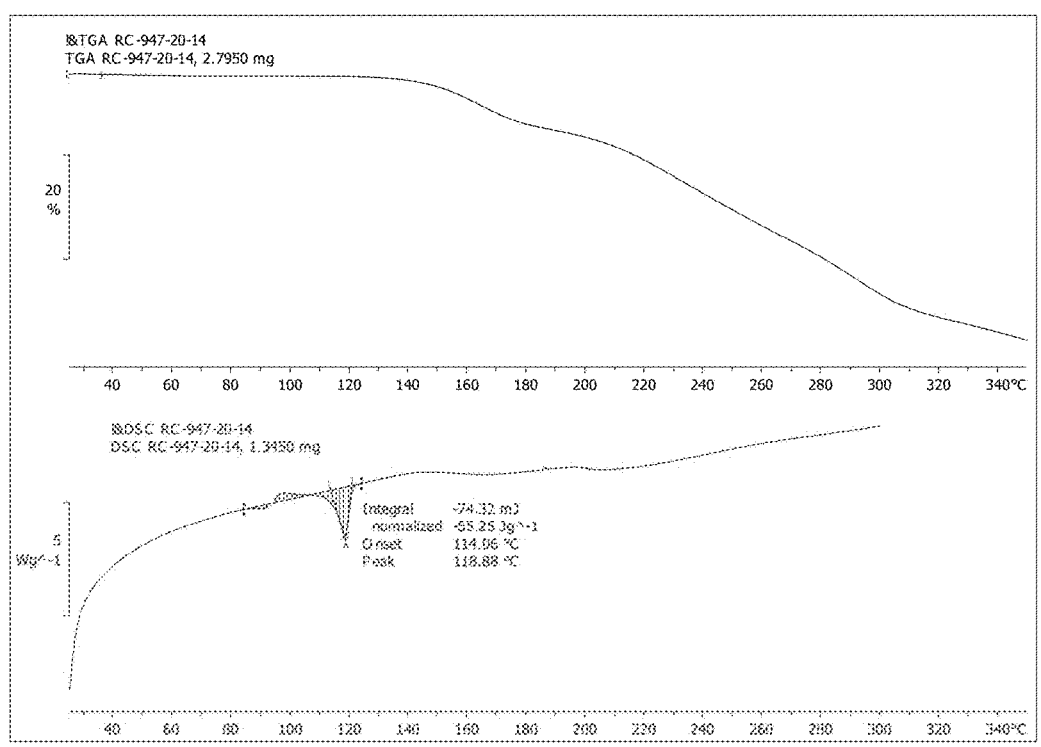

FIG. 27 shows the experimental differential scanning calorimetry (DSC) and Thermo-gravimetric Analysis (TGA) of TAF maleate.

DSC showed a small endotherm followed by exotherm followed by a main endotherm with onset 114° C. TGA showed no major weight loss upon heating.

Example 8

Preparation and Characterization of Tenofovir Alafenamide Ethanesulfonate

Tenofovir alafenamide free base was dissolved in 50 volumes of ethyl acetate (EtOAc) at room temperature, 1.1 eq. of 1M ethane sulfonic acid in THF was added. Precipitation was observed immediately. Filtration gave crystalline tenofovir alafenamide ethanesulfonate. Crystals with the same XRPD pattern were obtained similarly in IPA and THF.

NMR spectrum indicated 1 equivalent of ethane sulfonic acid.

The XRPD is shown in FIG. 14. Material exposed to stress condition (40° C. 75% RH for 14 days) showed no XRPD change.

Prominent peaks were selected from observed peaks by identifying substantially non-overlapping, low-angle peaks with strong intensity. The prominent peaks of tenofovir alafenamide ethanesulfonate include: 9.0, 9.9, 17.0, and 21.4±0.2° 2 Theta. The observed peaks of tenofovir alafenamide ethanesulfonate are shown in Table 8.

TABLE 8

Observed peaks in the XRPD pattern of tenofovir alafenamide ethanesulfonate

| No. | Pos. [°2Th.] | Rel. Int. [%] |
|---|---|---|
| 1 | 9.0 | 100 |
| 2 | 9.9 | 26 |
| 3 | 10.7 | 8 |

TABLE 8-continued

Observed peaks in the XRPD pattern of tenofovir alafenamide ethanesulfonate

| No. | Pos. [°2Th.] | Rel. Int. [%] |
|---|---|---|
| 4 | 17.0 | 37 |
| 5 | 18.8 | 37 |
| 6 | 19.6 | 26 |
| 7 | 21.4 | 58 |

Figure 28:
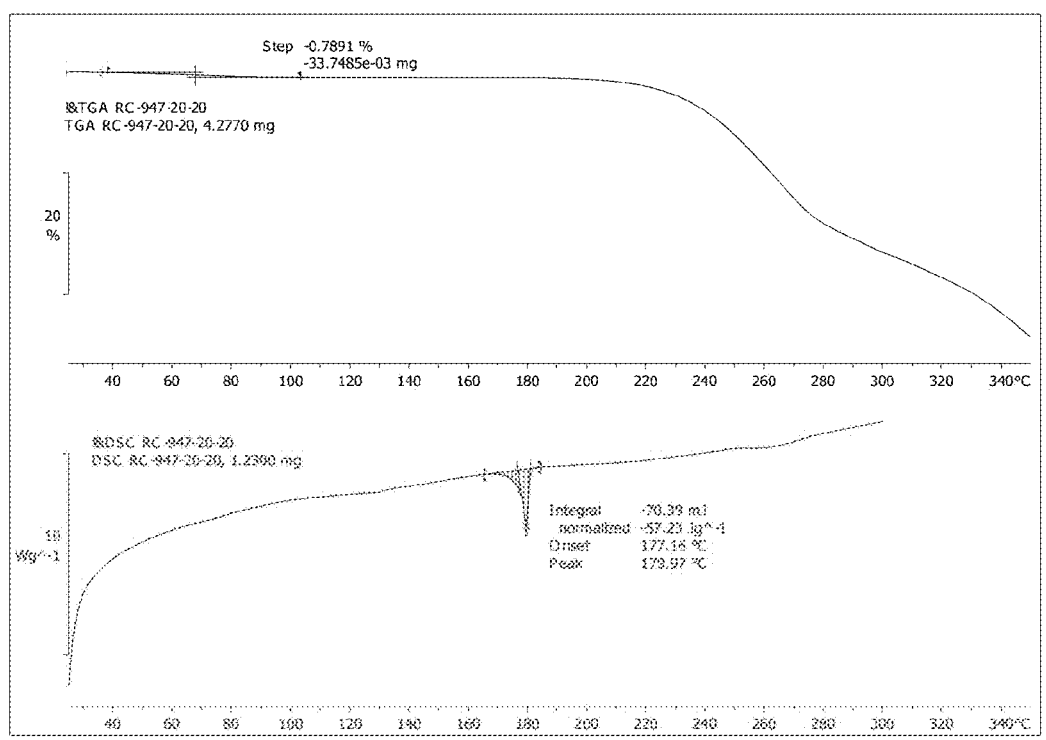

Presented in FIG. 28 is the experimental differential scanning calorimetry (DSC) and Thermo-gravimetric Analysis (TGA) of TAF ethanesulfonate.

DSC showed a sharp endotherm with onset of 177° C. TGA showed 0.8% weight loss upon heating from RT to 100° C.

Example 9

Preparation and Characterization of Tenofovir Alafenamide Benzenesulfonate

Tenofovir alafenamide free base was dissolved in 10 volumes of isopropyl alcohol (IPA) at room temperature, 1.1 eq. of 1M benzene sulfonic acid in THF was added. The mixture was a clear solution. The solvent was evaporated and MTBE was added to precipitate the solid. Filtration gave crystalline tenofovir alafenamide benzenesulfonate.

NMR spectrum indicated 1.0 equivalent of benzene sulfonic acid.

The XRPD is shown in FIG. 15. Material exposed to stress condition (40° C. 75% RH for 14 days) showed no change.

Crystals with the same XRPD were also obtained in other solvents such as EtOAc and THF. Prominent peaks were selected from observed peaks by identifying substantially non-overlapping, low-angle peaks with strong intensity. The prominent peaks of tenofovir alafenamide benzenesulfonate include: 4.1, 8.3, 13.3 and 17.8±0.2° 2 Theta. The observed peaks of tenofovir alafenamide benzenesulfonate are shown in Table 9.

TABLE 9

Observed peaks in the XRPD pattern of tenofovir alafenamide benzenesulfonate

| No. | Pos. [°2Th.] | Rel. Int. [%] |
|---|---|---|
| 1 | 4.1 | 33 |
| 2 | 6.5 | 6 |
| 3 | 8.3 | 100 |
| 4 | 11.9 | 5 |
| 5 | 13.3 | 25 |
| 6 | 14.7 | 6 |
| 7 | 15.4 | 11 |
| 8 | 16.5 | 16 |
| 9 | 17.8 | 53 |
| 10 | 18.9 | 25 |
| 11 | 19.4 | 28 |
| 12 | 20.3 | 50 |
| 13 | 21.1 | 46 |
| 14 | 23.1 | 44 |
| 15 | 24.1 | 28 |
| 16 | 24.9 | 34 |
| 17 | 29.2 | 12 |

Figure 29:
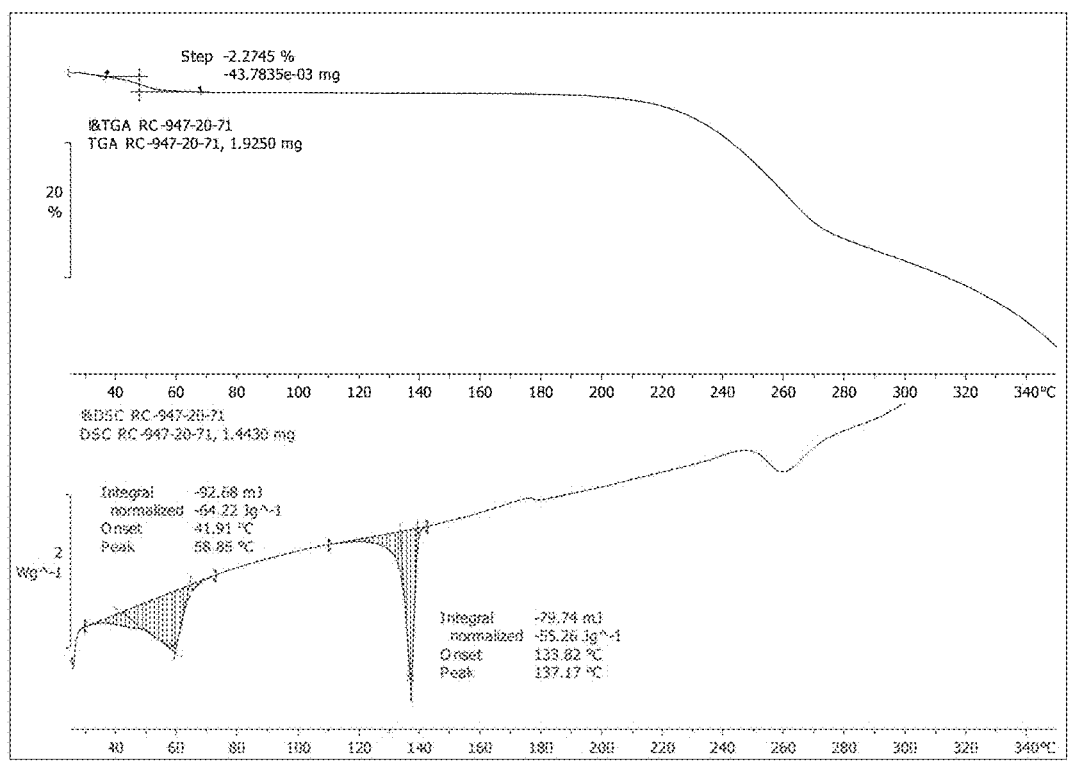

Presented in FIG. 29 is the experimental differential scanning calorimetry (DSC) and Thermo-gravimetric Analysis (TGA) of TAF benzenesulfonate.

DSC showed a broad endotherm with onset of 42° C. and a sharp endotherm with onset of 134° C. TGA showed 2.3% weight loss upon heating from RT to 70° C.

Example 10

Preparation and Characterization of Tenofovir Alafenamide Methanesulfonate

Tenofovir alafenamide free base was dissolved in 10 volumes of isopropyl alcohol (IPA) at room temperature, 1.1 eq. of 1M methane sulfonic acid in THF was added. Precipitation was observed upon acid addition. Filtration gave crystalline tenofovir alafenamide methanesulfonate.

NMR spectrum indicated 1:1 stoichiometry with methane sulfonic acid.

XRPD of tenofovir alafenamide methanesulfonate pattern 1 is shown in FIG. 16a. Prominent peaks were selected from observed peaks by identifying substantially non-overlapping, low-angle peaks with strong intensity. The prominent peaks of tenofovir alafenamide methanesulfonate pattern 1 include: 8.7, 9.9, 10.1, and 19.7±0.2° 2 Theta. The observed peaks of tenofovir alafenamide methanesulfonate pattern 1 are shown in Table 10a.

TABLE 10a

Observed peaks in the XRPD pattern 1 of tenofovir alafenamide methanesulfonate

| No. | Pos. [°2Th.] | Rel. Int. [%] |
|---|---|---|
| 1 | 4.1 | 3 |
| 2 | 8.7 | 61 |
| 3 | 9.9 | 100 |
| 4 | 10.1 | 82 |
| 5 | 13.2 | 8 |
| 6 | 17.2 | 79 |
| 7 | 18.8 | 79 |
| 8 | 19.7 | 99 |
| 9 | 20.4 | 91 |
| 10 | 21.7 | 42 |

Figure 30:
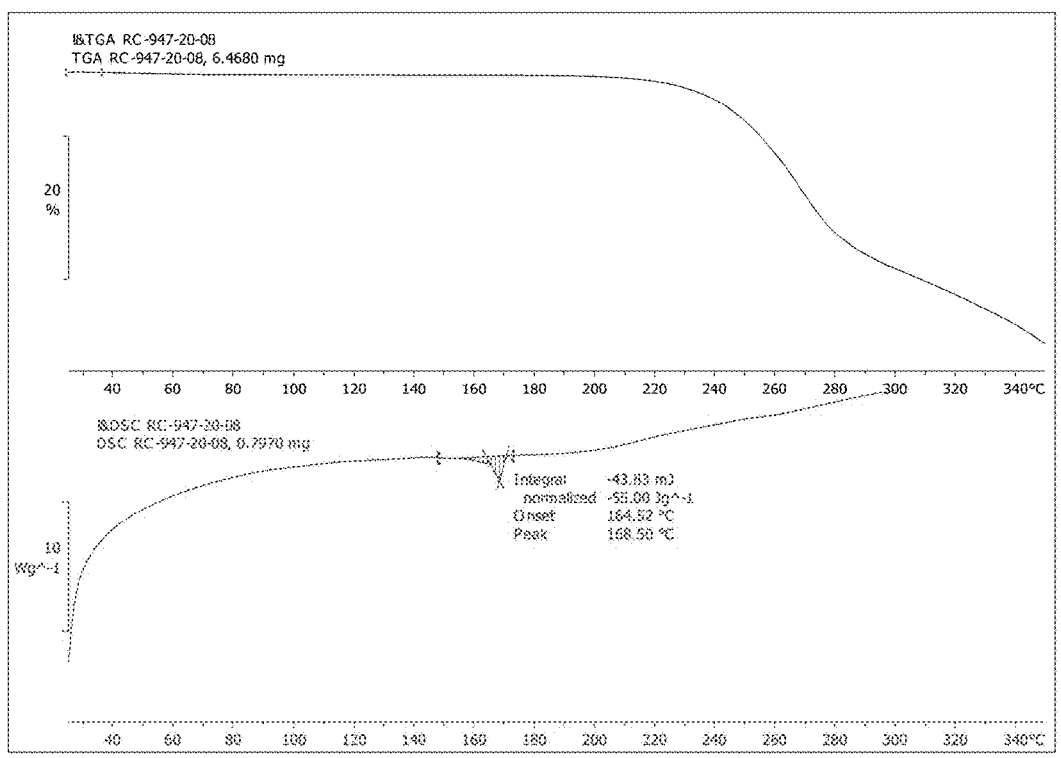

Presented in FIG. 30 is the experimental differential scanning calorimetry (DSC) and Thermo-gravimetric Analysis (TGA) of TAF methanesulfonate pattern 1.

DSC showed a sharp endotherm with onset of 164° C. TGA showed no weight loss upon heating from RT to 100° C.

Tenofovir alafenamide methanesulfonate pattern 1 changed to another form upon exposure to 40° C. 75% RH stress storage conditions for 14 days.

XRPD pattern 2 of tenofovir alafenamide methanesulfonate is shown in FIG. 16b. Prominent peaks were selected from observed peaks by identifying substantially non-overlapping, low-angle peaks with strong intensity. The prominent peaks of tenofovir alafenamide methanesulfonate pattern 2 include: 9.0, 9.5, 18.6, and 22.4±0.2° 2 Theta. The observed peaks of tenofovir alafenamide methanesulfonate pattern 2 are shown in Table 10b.

TABLE 10b

Observed peaks in the XRPD pattern 2 of tenofovir alafenamide methanesulfonate

| No. | Pos. [°2Th.] | Rel. Int. [%] |
|---|---|---|
| 1 | 4.5 | 44 |
| 2 | 6.8 | 10 |
| 3 | 9.0 | 100 |
| 4 | 9.5 | 50 |
| 5 | 12.4 | 10 |
| 6 | 12.9 | 16 |
| 7 | 13.3 | 10 |
| 8 | 15.9 | 12 |
| 9 | 17.9 | 40 |
| 10 | 18.6 | 97 |
| 11 | 19.0 | 60 |
| 12 | 19.8 | 10 |
| 13 | 20.9 | 62 |
| 14 | 22.4 | 74 |
| 15 | 23.4 | 12 |
| 16 | 24.2 | 23 |
| 17 | 27.0 | 30 |

Example 11

Preparation and Characterization of Tenofovir Alafenamide Mucate

Tenofovir alafenamide free base was dissolved in 50 volumes of ethyl acetate at room temperature, 1 eq. of 1M mucic acid in THF was added. The solution was cooled down below room temperature. Small amount of solid precipitated out of this solvent system. Pattern 1 was obtained from salt formation in EtOAc and THF.

Pattern 2 was obtained using a similar procedure in IPA.

XRPD patterns of tenofovir alafenamide mucate Pattern 1 and Pattern 2 are shown in FIGS. 10 and 11.

NMR spectra of both Patterns show a 1:2 tenofovir alafenamide: mucic acid stoichiometry ratio.

Material exposed to stress condition (40° C. 75% RH for 14 days) showed no change for both patterns.

Prominent peaks were selected from observed peaks by identifying substantially non-overlapping, low-angle peaks with strong intensity. The prominent peaks of tenofovir alafenamide mucate pattern 1 include: 6.4, 7.2, 18.1, and 19.5±0.2° 2 Theta. The observed peaks of tenofovir alafenamide mucate pattern 1 are shown in Table 11.

TABLE 11

Observed peaks in the XRPD pattern of tenofovir alafenamide mucate pattern 1

| No. | Pos. [°2Th.] | Rel. Int. [%] |
|---|---|---|
| 1 | 3.8 | 37 |
| 2 | 4.3 | 45 |
| 3 | 6.4 | 19 |
| 4 | 7.2 | 20 |
| 5 | 8.4 | 15 |
| 6 | 10.6 | 9 |
| 7 | 11.7 | 11 |
| 8 | 12.8 | 11 |
| 9 | 18.1 | 35 |
| 10 | 19.5 | 100 |
| 11 | 21.0 | 36 |

TABLE 11-continued

Observed peaks in the XRPD pattern of tenofovir alafenamide mucate pattern 1

| No. | Pos. [°2Th.] | Rel. Int. [%] |
|---|---|---|
| 12 | 22.9 | 15 |
| 13 | 26.9 | 33 |

The prominent peaks of tenofovir alafenamide mucate pattern 2 include: 8.5, 9.9, 16.9, and 21.1±0.2° 2 Theta. The observed peaks of tenofovir alafenamide mucate pattern 2 are shown in Table 12.

TABLE 12

Observed peaks in the XRPD pattern of tenofovir alafenamide mucate pattern 2

| No. | Pos. [°2Th.] | Rel. Int. [%] |
|---|---|---|
| 1 | 4.2 | 85 |
| 2 | 6.7 | 5 |
| 3 | 8.5 | 43 |
| 4 | 9.9 | 24 |
| 5 | 13.3 | 11 |
| 6 | 16.9 | 80 |
| 7 | 18.6 | 25 |
| 8 | 19.6 | 43 |
| 9 | 21.1 | 100 |
| 10 | 22.9 | 40 |
| 11 | 26.2 | 66 |
| 12 | 29.2 | 44 |

Figure 31:
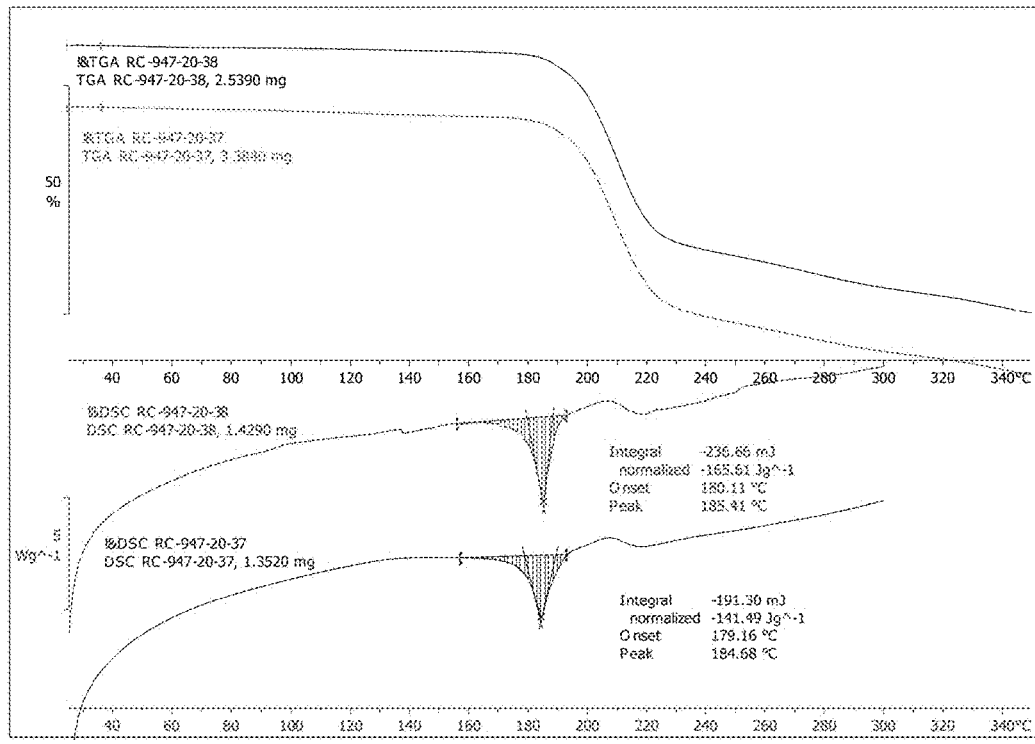
FIG. 31. Presented in FIG. 31 is the experimental differential scanning calorimetry (DSC) and Thermo-gravimetric Analysis (TGA) of TAF mucate Pattern 1 (RC-947-20-38) and Pattern 2 (RC-947-20-37)

Presented in FIG. 31 is the experimental differential scanning calorimetry (DSC) and Thermo-gravimetric Analysis (TGA) of TAF mucate Pattern 1 (RC-947-20-38) and Pattern 2 (RC-947-20-37).

Pattern 1 has an endotherm with onset of 180° C. Pattern 2 has an endotherm with onset of 179° C. TGA showed no weight loss upon heating from RT to 100° C. for both materials.

Example 12

Preparation and Characterization of Tenofovir Alafenamide Sesquifumarate IPA Solvate 1.92 g of tenofovir alafenamide free base was stirred with 0.696 g (1.5 equivalents) of fumaric acid in 30 mL isopropanol at about 60° C. to dissolve. The solution was filtered, cooled to about 21° C., and stirred for about 16 hours to form a slurry. The solid was filtered and washed with 3 mL isopropanol. The wet cake was analyzed by XRPD to give tenofovir alafenamide sesquifumarate IPA solvate (pattern 1). The solids were dried at about 50 to 60° C. for one day and XRPD of the dried solids showed tenofovir alafenamide sesquifumarate Pattern 5. HPLC analysis of the solids showed 26.7% fumaric acid.

The XRPD of tenofovir alafenamide sesquifumarate IPA solvate (pattern 1) is shown in FIG. 1.

Prominent peaks were selected from observed peaks by identifying substantially non-overlapping, low-angle peaks with strong intensity. The prominent peaks of tenofovir alafenamide sesquifumarate IPA solvate include: 4.5, 20.4, 26.5, and 26.9±0.2° 2 Theta. The observed peaks of tenofovir alafenamide sesquifumarate IPA solvate are shown in Table 13.

TABLE 13

Observed peaks in the XRPD pattern of tenofovir alafenamide sesquifumarate IPA solvate (pattern 1)

| No. | Pos. [°2Th.] | Rel. Int. [%] |
|---|---|---|
| 1 | 4.5 | 54 |
| 2 | 11.8 | 2 |
| 3 | 13.2 | 9 |
| 4 | 14.1 | 2 |
| 5 | 16.7 | 3 |
| 6 | 18.3 | 18 |
| 7 | 19.8 | 9 |
| 8 | 20.4 | 41 |
| 9 | 22.0 | 67 |
| 10 | 22.6 | 61 |
| 11 | 23.9 | 6 |
| 12 | 24.3 | 5 |
| 13 | 25.9 | 7 |
| 14 | 26.5 | 81 |
| 15 | 26.9 | 100 |
| 16 | 29.1 | 3 |
| 17 | 29.7 | 2 |
| 18 | 31.0 | 30 |
| 19 | 31.4 | 23 |
| 20 | 32.6 | 1 |
| 21 | 33.6 | 4 |
| 22 | 35.9 | 2 |
| 23 | 37.1 | 2 |
| 24 | 39.0 | 2 |

Figure 21:
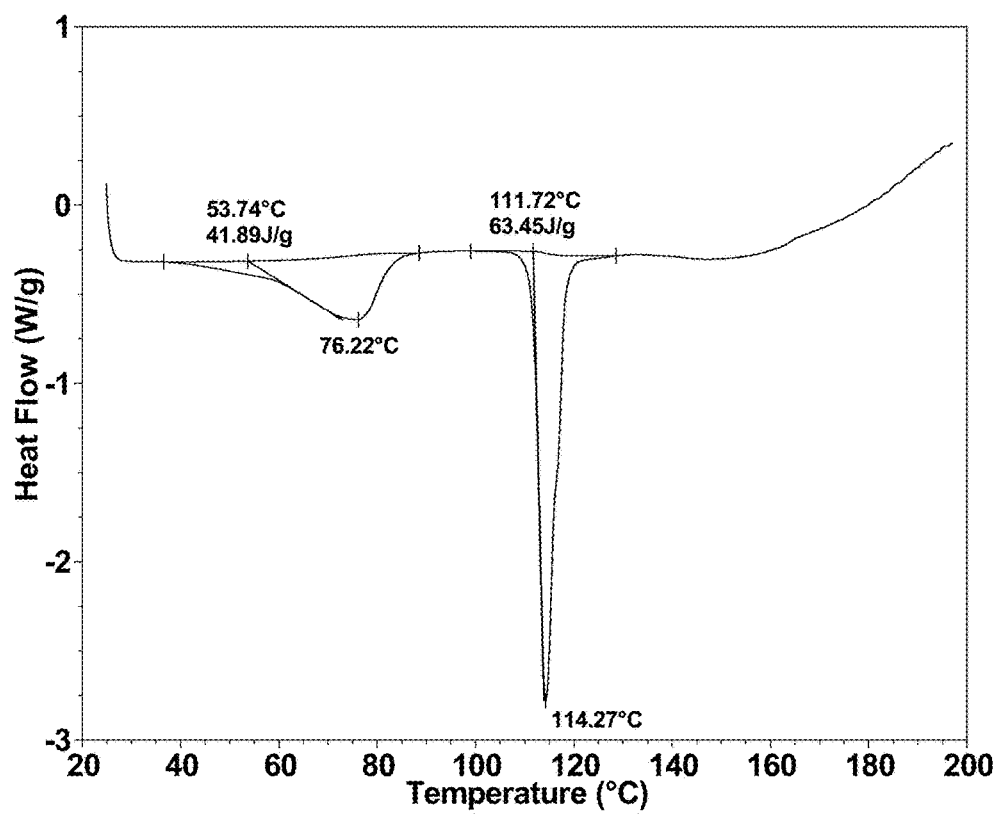

FIG. 21 shows the experimental differential scanning calorimetry (DSC) of TAF sesquifumarate isopropanol solvate.

DSC showed two endotherms with onset of 54° C. corresponding to solvent loss (IPA), and 112° C.

Figure 33:
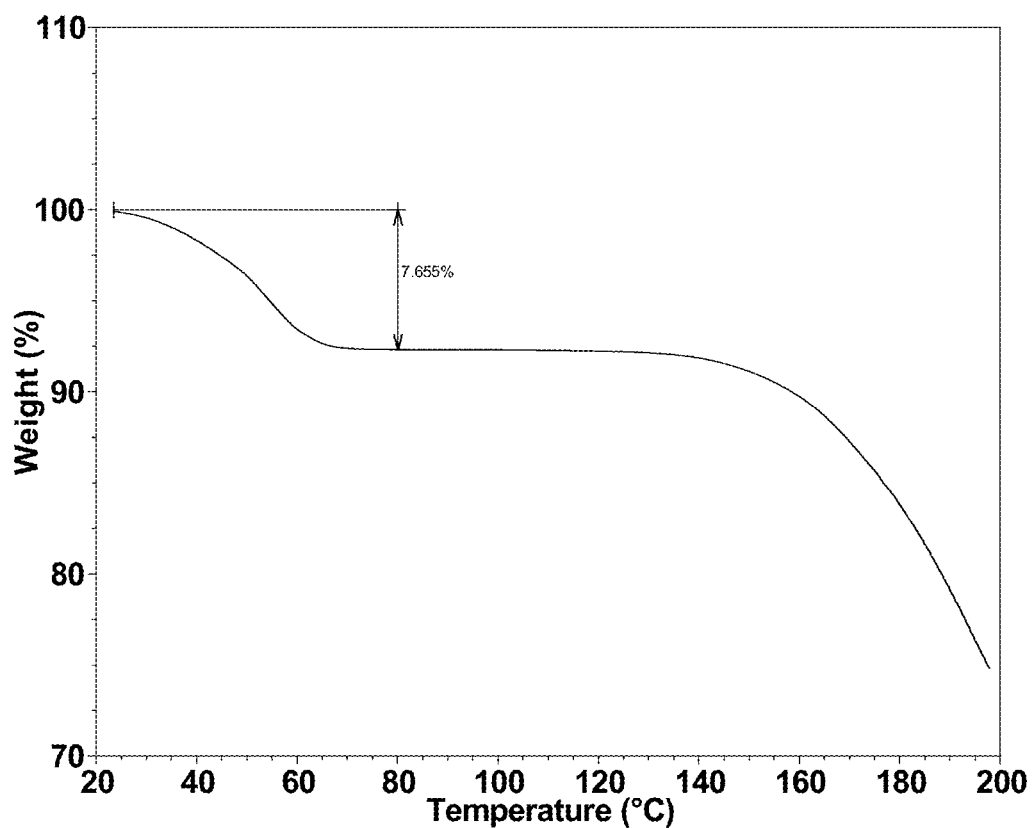

Presented in FIG. 33 is the experimental Thermo-gravimetric Analysis of tenofovir alafenamide sesquifumarate IPA solvate (pattern 1).

TGA showed about 7.7% weight loss between RT and 80° C.

After drying at 50° C. under vacuum for half an hour, the IPA solvate became Pattern 5, a non-solvated form.

Example 13

Preparation and Characterization of Tenofovir Alafenamide Sesquifumarate MEK Solvate A sample of non-solvated TAF sesquifumarate (Pattern 5, see example 16), about 50 mg, was stirred in 1 mL MEK at about 21° C. for about one day. The XRPD of the wet sample showed Pattern 2, which converted to pattern 5 after drying at 65° C. under vacuum for 1 day. The XRPD of tenofovir alafenamide sesquifumarate MEK solvate (pattern 2) is shown in FIG. 2.

Prominent peaks were selected from observed peaks by identifying substantially non-overlapping, low-angle peaks with strong intensity. The prominent peaks of tenofovir alafenamide sesquifumarate MEK solvate include: 4.6, 22.8, 27.4, and 27.8±0.2° 2 Theta. The observed peaks of tenofovir alafenamide sesquifumarate MEK solvate are shown in Table 14.

TABLE 14

Observed peaks in the XRPD pattern of tenofovir alafenamide sesquifumarate MEK solvate (pattern 2)

| No. | Pos. [°2Th.] | Rel. Int. [%] |
|---|---|---|
| 1 | 4.6 | 37 |
| 2 | 10.6 | 3 |
| 3 | 11.3 | 7 |
| 4 | 11.9 | 4 |
| 5 | 12.4 | 5 |
| 6 | 13.6 | 9 |
| 7 | 15.0 | 3 |
| 8 | 15.3 | 7 |
| 9 | 16.2 | 3 |
| 10 | 17.1 | 2 |
| 11 | 17.6 | 3 |
| 12 | 18.2 | 7 |
| 13 | 18.7 | 11 |
| 14 | 19.1 | 7 |
| 15 | 19.5 | 3 |
| 16 | 20.4 | 9 |
| 17 | 20.7 | 15 |
| 18 | 21.1 | 18 |
| 19 | 22.4 | 21 |
| 20 | 22.8 | 100 |
| 21 | 23.3 | 39 |
| 22 | 24.5 | 13 |
| 23 | 27.4 | 98 |
| 24 | 27.8 | 94 |
| 25 | 30.1 | 5 |
| 26 | 32.0 | 28 |
| 27 | 32.4 | 8 |
| 28 | 33.6 | 1 |
| 29 | 34.8 | 3 |
| 30 | 37.0 | 2 |

Figure 34:
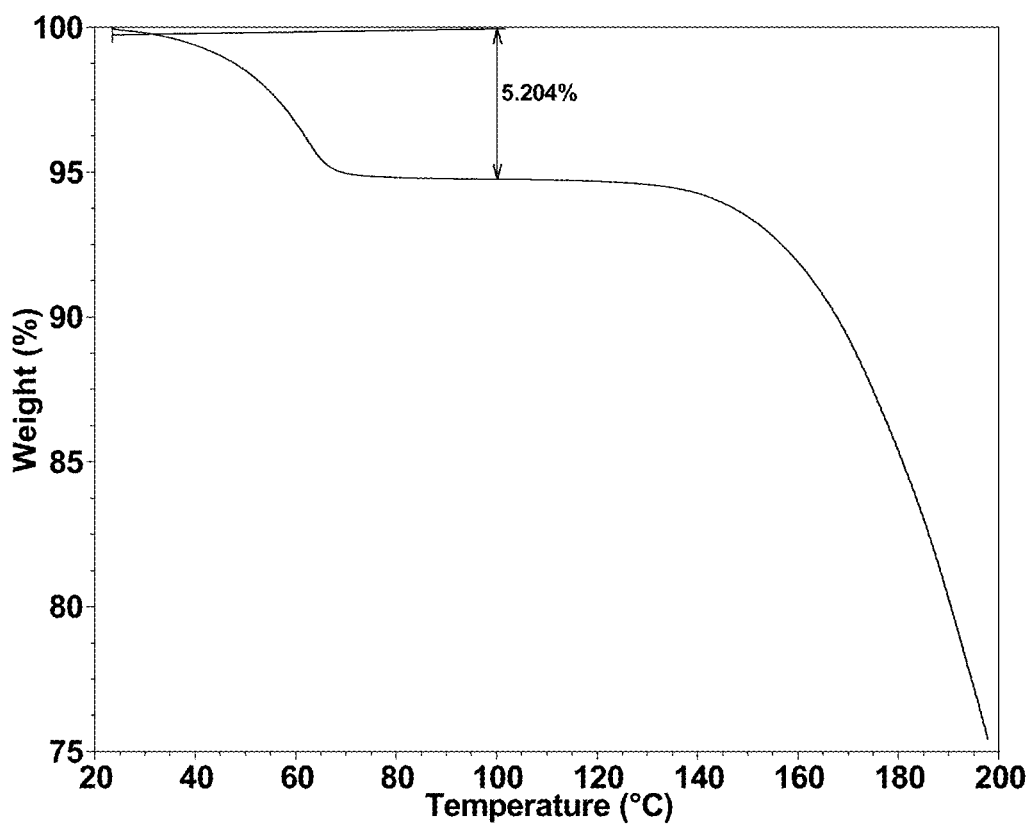
FIG. 34. Presented in FIG. 34 is the experimental Thermo-gravimetric Analysis of tenofovir alafenamide sesquifumarate MEK solvate (pattern 2)

Presented in FIG. 34 is the experimental Thermo-gravimetric Analysis of tenofovir alafenamide sesquifumarate MEK solvate (pattern 2).

TGA showed about 5.2% weight loss between RT and 100° C.

After drying at about 50° C. under vacuum for about half an hour, the MEK solvate became Pattern 5, a non-solvated form.

Example 14

Preparation and Characterization of Tenofovir Alafenamide Sesquifumarate THF Solvate 500 mg of tenofovir alafenamide free base was stirred with 365.4 mg (3 equivalents) of fumaric acid in 5 mL THF at about 70° C. to dissolve. The solution was filtered, cooled to 21° C., and stirred with seeds of TAF sesquifumarate IPA solvate for about 16 hours to form a thin slurry. The sample was evaporated at about 21° C. under vacuum to about 2.5 mL, and a thick slurry was obtained. The slurry was stirred for 1 hour, and XRPD analysis showed it had a unique pattern (Pattern 3).

In another experiment, 2 g of tenofovir alafenamide free base was stirred with 1.46 g (3 equivalents) of fumaric acid in 15 mL THF at about 70° C. to dissolve. The solution was filtered, cooled to about 21° C., and stirred with seeds of TAF sesquifumarate THF solvate (obtained in the previous experiment) for about 30 min to form a thin slurry. The sample was evaporated at about 21° C. under vacuum to about 10 mL, and a thick slurry was obtained. The slurry was stirred for about 16 hours, and XRPD analysis showed it was consistent with Pattern 3. The solids were isolated by filtration, washing with a mixture of THF and heptane (1:1 mixture, 2 mL) and heptane (2 mL). The solids were dried at about 65° C. under vacuum for about 1 day. XRPD showed it converted to TAF sesquifumarate Pattern 5. HPLC analysis of the solids showed 27.3% fumaric acid.

The XRPD of tenofovir alafenamide sesquifumarate THF solvate (pattern 3) is shown in FIG. 3.

Prominent peaks were selected from observed peaks by identifying substantially non-overlapping, low-angle peaks with strong intensity. The prominent peaks of tenofovir alafenamide sesquifumarate THF solvate include: 4.5, 22.6, 27.2, and 27.7±0.2° 2 Theta. The observed peaks of tenofovir alafenamide sesquifumarate THF solvate are shown in Table 15.

TABLE 15

Observed peaks in the XRPD pattern of tenofovir alafenamide sesquifumarate THF solvate (pattern 3)

| No. | Pos. [°2Th.] | Rel. Int. [%] |
|---|---|---|
| 1 | 4.5 | 39 |
| 2 | 10.5 | 2 |
| 3 | 11.2 | 6 |
| 4 | 11.9 | 3 |
| 5 | 12.3 | 2 |
| 6 | 13.5 | 5 |
| 7 | 15.3 | 4 |
| 8 | 16.3 | 1 |
| 9 | 18.2 | 5 |
| 10 | 18.6 | 11 |
| 11 | 20.2 | 15 |
| 12 | 20.9 | 18 |
| 13 | 22.6 | 100 |
| 14 | 23.1 | 37 |
| 15 | 24.4 | 11 |
| 16 | 27.2 | 76 |
| 17 | 27.7 | 74 |
| 18 | 29.9 | 2 |
| 19 | 30.9 | 2 |
| 20 | 31.8 | 23 |
| 21 | 34.6 | 3 |
| 22 | 36.7 | 2 |
| 23 | 38.0 | 1 |

Figure 35:
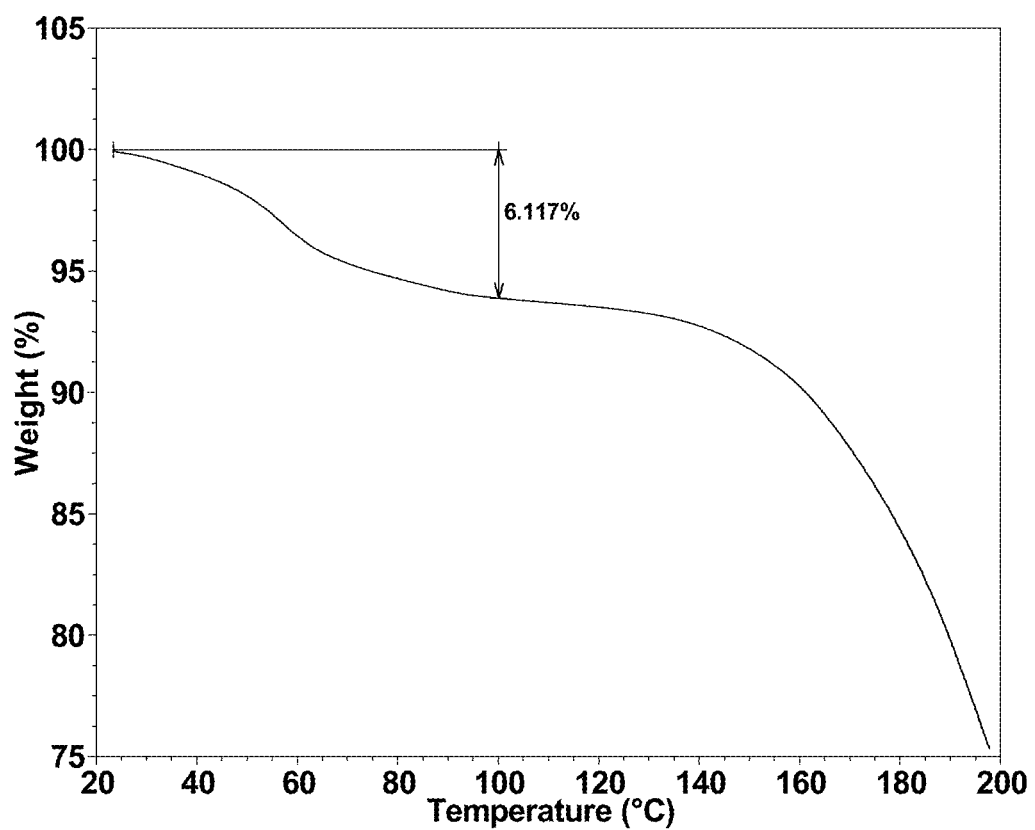
FIG. 35. Presented in FIG. 35 is the experimental Thermo-gravimetric Analysis of tenofovir alafenamide sesquifumarate THF solvate (pattern 3)

Presented in FIG. 35 is the experimental Thermo-gravimetric Analysis of tenofovir alafenamide sesquifumarate THF solvate (pattern 3).

The TGA thermogram of TAF sesquifumarate THF solvate showed about 6.1% weight loss between RT and 100° C. After drying at about 65° C. under vacuum for about one day, the THF solvate became Pattern 5, a non-solvated form.

Example 15

Preparation and Characterization of Tenofovir Alafenamide Sesquifumarate Acetone Solvate 1 g of tenofovir alafenamide free base was stirred with 487.2 mg (2 equivalents) of fumaric acid in about 15 mL acetone at about 55° C. to dissolve. The solution was filtered, cooled to about 21° C., and stirred for about 16 hours to form a slurry. XRPD analysis showed it had a unique pattern (Pattern 4).

The XRPD of tenofovir alafenamide sesquifumarate acetone solvate (pattern 4) is shown in FIG. 4.

Prominent peaks were selected from observed peaks by identifying substantially non-overlapping, low-angle peaks with strong intensity. The prominent peaks of tenofovir alafenamide sesquifumarate acetone solvate include: 4.6, 22.9, 27.6 and 28.0±0.2° 2 Theta. The observed peaks of tenofovir alafenamide sesquifumarate acetone solvate are shown in Table 16.

TABLE 16

Observed peaks in the XRPD pattern of tenofovir alafenamide sesquifumarate acetone solvate (pattern 4)

| No. | Pos. [°2Th.] | Rel. Int. [%] |
|---|---|---|
| 1 | 4.6 | 75 |
| 2 | 10.5 | 4 |
| 3 | 11.3 | 9 |
| 4 | 12.4 | 5 |
| 5 | 13.7 | 13 |
| 6 | 15.4 | 8 |
| 7 | 17.2 | 3 |
| 8 | 17.6 | 4 |
| 9 | 18.3 | 10 |
| 10 | 19.1 | 13 |
| 11 | 20.5 | 10 |
| 12 | 20.8 | 16 |
| 13 | 21.2 | 18 |
| 14 | 22.5 | 22 |
| 15 | 22.9 | 100 |
| 16 | 23.5 | 50 |
| 17 | 24.6 | 12 |
| 18 | 27.6 | 87 |
| 19 | 28.0 | 72 |
| 20 | 30.3 | 5 |
| 21 | 32.3 | 21 |

Figure 36:
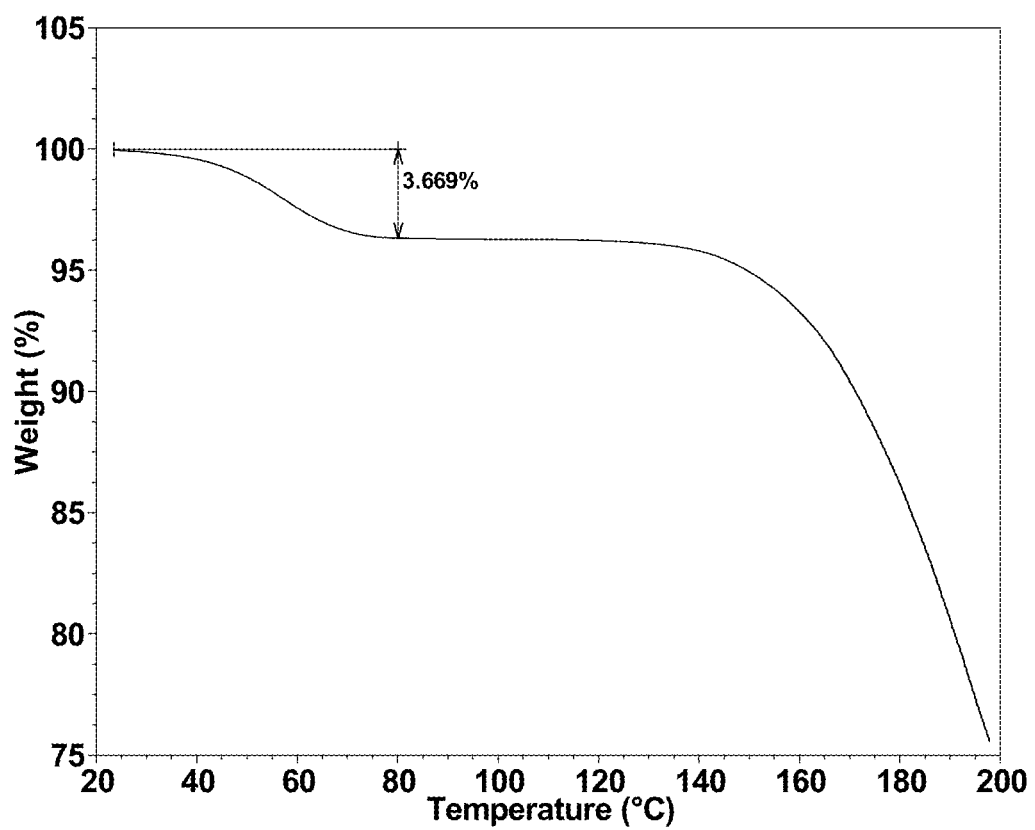
FIG. 36. Presented in FIG. 36 is the experimental Thermo-gravimetric Analysis of tenofovir alafenamide sesquifumarate acetone solvate (pattern 4)

Presented in FIG. 36 is the experimental Thermo-gravimetric Analysis of tenofovir alafenamide sesquifumarate acetone solvate (pattern 4).

The TGA thermogram of TAF sesquifumarate acetone solvate showed about 3.7% weight loss between RT and 80° C. After drying at about 45° C. under vacuum for 4 hours, the THF solvate become Pattern 5, a non-solvated form.

Example 16

Preparation and Characterization of Tenofovir Alafenamide Sesquifumarate (Non-Solvate Form)

This form was obtained by drying TAF sesquifumarate IPA solvate, MEK solvate, or THF solvate, as described earlier.

The XRPD of tenofovir alafenamide sesquifumarate (pattern 5) is shown in FIG. 5. Prominent peaks were selected from observed peaks by identifying substantially non-overlapping, low-angle peaks with strong intensity. The prominent peaks of tenofovir alafenamide sesquifumarate include: 5.0, 20.1, 22.7, and 25.2±0.2° 2 Theta. The observed peaks of tenofovir alafenamide sesquifumarate are shown in Table 17.

TABLE 17

Observed peaks in the XRPD pattern of tenofovir alafenamide sesquifumarate (pattern 5)

| No. | Pos. [°2Th.] | Rel. Int. [%] |
|---|---|---|
| 1 | 5.0 | 100 |
| 2 | 10.6 | 3 |
| 3 | 11.0 | 1 |
| 4 | 15.0 | 7 |
| 5 | 16.2 | 1 |
| 6 | 17.9 | 3 |
| 7 | 18.8 | 1 |
| 8 | 20.1 | 19 |
| 9 | 22.7 | 23 |
| 10 | 24.5 | 34 |
| 11 | 25.2 | 39 |

TABLE 17-continued

Observed peaks in the XRPD pattern of tenofovir alafenamide sesquifumarate (pattern 5)

| No. | Pos. [°2Th.] | Rel. Int. [%] |
|---|---|---|
| 12 | 27.7 | 14 |
| 13 | 28.9 | 7 |
| 14 | 29.4 | 9 |
| 15 | 30.3 | 9 |
| 16 | 32.9 | 2 |

Figure 37:
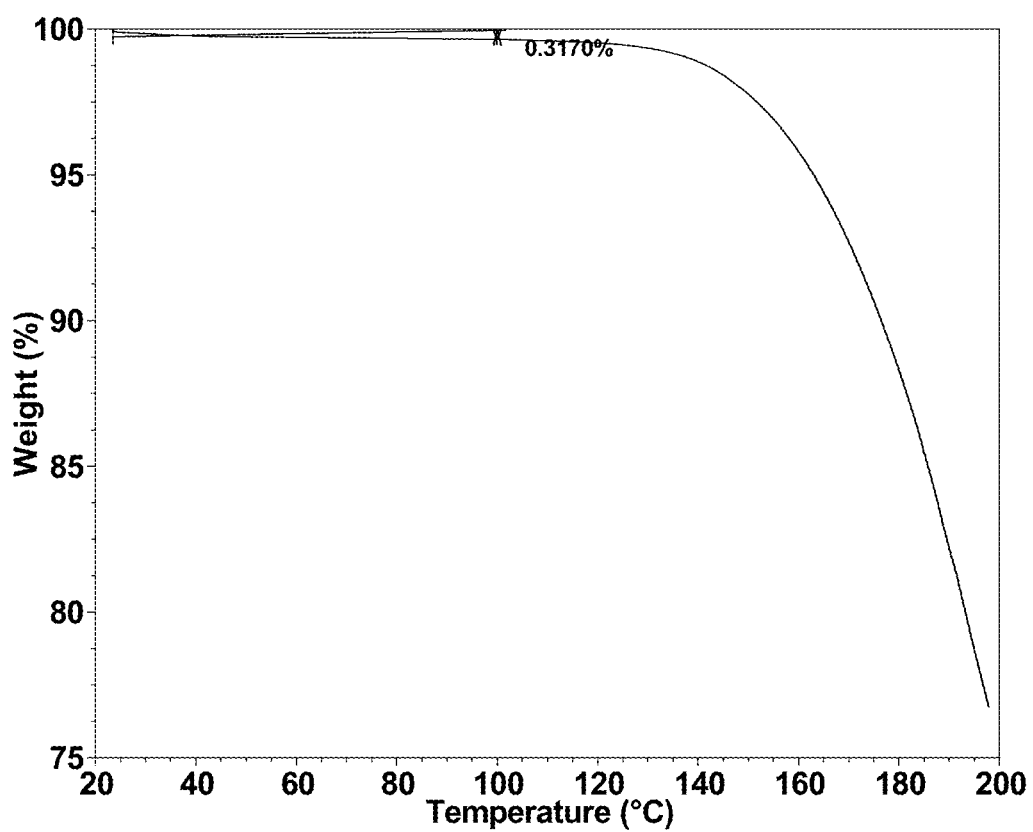
FIG. 37. Presented in FIG. 37 is the experimental Thermo-gravimetric Analysis of tenofovir alafenamide sesquifumarate (pattern 5)

Presented in FIG. 37 is the experimental Thermo-gravimetric Analysis of tenofovir alafenamide sesquifumarate (pattern 5).

The TGA thermogram of TAF sesquifumarate Pattern 5 showed insignificant weight loss (0.31%) between RT and 100° C., indicating it is a non-solvated form.

Figure 22:
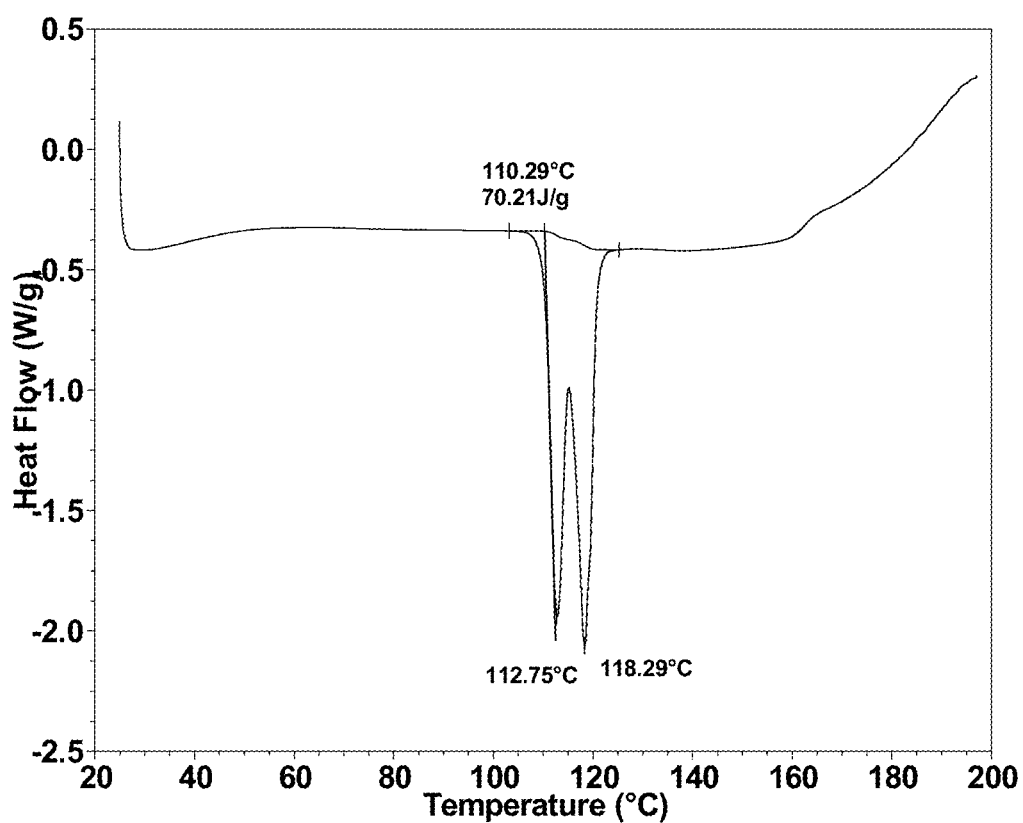

FIG. 22 shows the experimental differential scanning calorimetry (DSC) of TAF sesquifumarate.

DSC showed two endotherm onsets of 110° C. corresponding to melting of Pattern 5 and another melting event at 118° C.

Example 17

Preparation and Characterization of Tenofovir Alafenamide p-Toluene Sulfonate

Tenofovir alafenamide free base was dissolved in 10 volumes of isopropyl alcohol (IPA). 1 equivalent of 1M p-toluene sulfonic acid in THF was added. Some solvent was evaporated and 50 volumes of MTBE were added to precipitate the crystalline salt.

NMR spectrum showed a 1:1 stoichiometry ratio of p-toluene sulfonic acid to tenofovir alafenamide.

Figure 32:
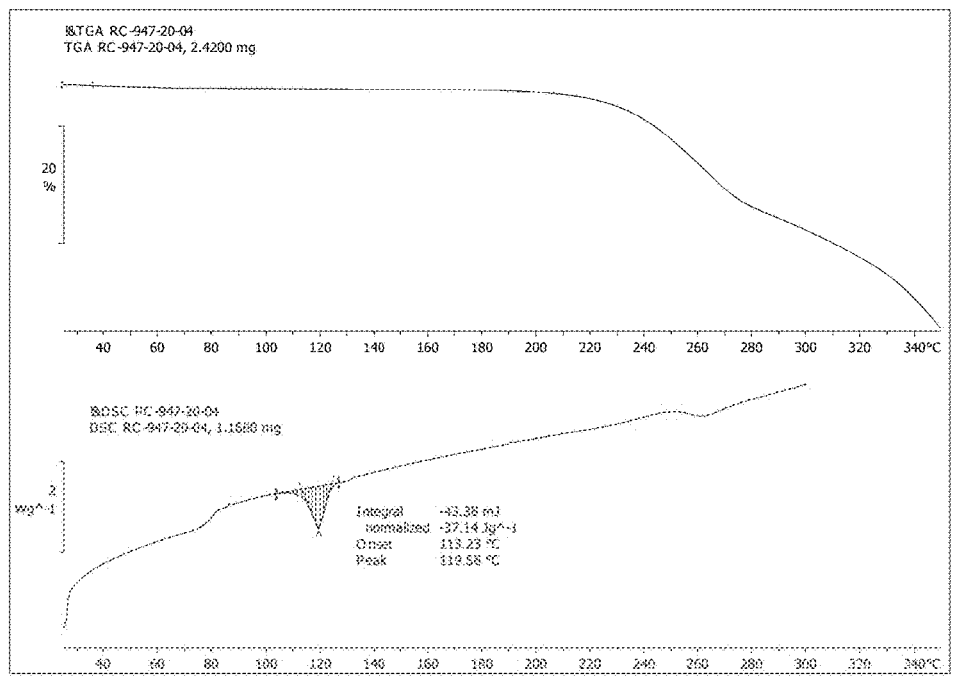
FIG. 32. Presented in FIG. 32 is the experimental differential scanning calorimetry (DSC) and Thermo-gravimetric Analysis (TGA) of TAF p-toluene sulfonate FIG. 33. Presented in FIG. 33 is the experimental Thermo-gravimetric Analysis of tenofovir alafenamide sesquifumarate IPA solvate (pattern 1)

DSC and TGA thermograms of TAF p-toluene sulfonate are shown in FIG. 32.

Example 18

Tenofovir alafenamide free base was dissolved in 50 volumes of ethyl acetate (EtOAc). 1 equivalent of a 1M ketoglutaric acid THF solution was added, followed by cooling at sub-ambient temperature. A small amount of solid precipitated out of this solvent system. The sample deliquesced prior to analysis.

Example 19

Preparation and Characterization of Tenofovir Alafenamide Nicotinate

Tenofovir alafenamide free base was dissolved in 10 volumes of isopropyl alcohol (IPA) at room temperature, 1.1 equivalent of a 1M solution of nicotinic acid in THF was added. The mixture was a clear solution. The solvent was cooled to sub-ambient temperature and precipitation was observed.

Example 20

The following acids were screened to identify new salts, co-crystals and forms in 3 different solvents (THF, EtOAc, IPA) with a similar protocol as in examples 1-19: 2,5-Dihydroxybenzoic acid, 4 hydroxy benzoic acid, pamoic acid, and (S)-(−)-lactamide, D-Glucoheptonic acid, benzoic acid, acetic acid, propionic acid, orotic acid, L-aspartic acid, cholic acid, isophthalic acid, benzamide, nicotinamide, tromethamine, and N-methyl-D-glucamine.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A solvate of tenofovir alafenamide sesquifumarate, wherein the solvate comprises a solvent selected from the group consisting of isopropanol, methyl ethyl ketone, tetrahydrofuran and acetone.

2. A crystal form of the sesquifumarate of claim 1, wherein the solvent is isopropanol and the crystal form has an XRPD pattern comprising 2theta values of 4.5±0.2, 20.4±0.2, 26.5±0.2, and 26.9±0.2.

3. A crystal form of the sesquifumarate of claim 1, wherein the solvent is isopropanol and the crystal form has a differential scanning calorimetry (DSC) comprising onset endotherms of 54±2° C. and 112±2° C.

4. A crystal form of the sesquifumarate of claim 1, wherein the solvent is methyl ethyl ketone and the crystal form has a XRPD pattern comprising 2theta values of 4.6±0.2, 22.8±0.2, 27.4±0.2, and 27.8±0.2.

5. A crystal form of the sesquifumarate of claim 1, wherein the solvent is tetrahydrofuran and the crystal form has a XRPD pattern comprising 2theta values of 4.5±0.2, 22.6±0.2, 27.2±0.2, and 27.7±0.2.

6. A crystal form of the sesquifumarate of claim 1, wherein the solvent is acetone and the crystal form has a XRPD pattern comprising 2theta values of 4.6±0.2, 22.9±0.2, 27.6±0.2 and 28.0±0.2.

7. A crystal form of tenofovir alafenamide sesquifumarate, wherein the crystal form has a XRPD pattern comprising 2theta values of 5.0±0.2, 20.1±0.2, 22.7±0.2, and 25.2±0.2.

8. A crystal form of tenofovir alafenamide sesquifumarate, having differential scanning calorimetry (DSC) onset endotherms of 110±2° C. and 118±2° C.

9. A pharmaceutical composition comprising the crystal form of claim 7 and a pharmaceutically acceptable excipient.

10. A method for treating an HIV infection comprising administering to a subject in need thereof a therapeutically effective amount of the pharmaceutical composition of claim 4.

11. A pharmaceutical composition comprising the crystal form of claim 8 and a pharmaceutically acceptable excipient.

12. A method for treating an HIV infection comprising administering to a subject in need thereof a therapeutically effective amount of the pharmaceutical composition of claim 11.

* * * * *